(12) United States Patent
Askew et al.

(10) Patent No.: US 7,625,755 B2
(45) Date of Patent: Dec. 1, 2009

(54) CONDITIONAL KNOCKOUT METHOD FOR GENE TRAPPING AND GENE TARGETING USING AN INDUCIBLE GENE SILENCER

(75) Inventors: G. Roger Askew, Boxford, MA (US); Kim L. Kanki, Boxford, MA (US)

(73) Assignee: Wyeth, Madison, NJ (US)

( * ) Notice: Subject to any disclaimer, the term of this patent is extended or adjusted under 35 U.S.C. 154(b) by 82 days.

(21) Appl. No.: 10/448,395

(22) Filed: May 30, 2003

(65) Prior Publication Data

US 2004/0241851 A1    Dec. 2, 2004

(51) Int. Cl.
C12N 15/87 (2006.01)
C12N 15/63 (2006.01)
C12N 15/11 (2006.01)

(52) U.S. Cl. .................... 435/462; 435/320.1; 536/23.1

(58) Field of Classification Search .................. None
See application file for complete search history.

(56) References Cited

U.S. PATENT DOCUMENTS

| | | | | |
|---|---|---|---|---|
| 6,136,566 A | 10/2000 | Sands et al. | ................ | 435/69.7 |
| 2004/0018624 A1* | 1/2004 | Harrington et al. | .......... | 435/455 |

FOREIGN PATENT DOCUMENTS

| | | | |
|---|---|---|---|
| WO | WO 00/56874 | * | 9/2000 |
| WO | WO 01/29208 | * | 4/2001 |

OTHER PUBLICATIONS

Albert, Henrik, et al., "Site-specific integration of DNA into wild-type and mutant lox sites placed in the plant genome", The Plant Journal, 1995, vol. 7(4), pp. 649-659.
Araki, Kimi, et al., "Exchangeable gene trap using the Cre/mutated Lox system", Cellular and Molecular Biology, 1999, vol. 45(5), pp. 737-750.
Chappell, Stephen A., et al., "A 9-nt segment of a cellular mRNA can function as an internal ribosome entry site (IRES) and when present in linked multiple copies greatly enhances IRES activity", PNAS, Feb. 15, 2000, vol. 97, No. 4, pp. 1536-1541.
Doetschman, Thomas, et al., "Targetted correction of a mutant HPRT gene in mouse embryonic stem cells", Nature, Dec. 10, 1987, vol. 330, pp. 576-578.
Friedrich, Glenn, et al., "Promoter traps in embryonic stem cells: a genetics screen to identify and mutate developmental genes in mice," Genes and Development, 1991, vol. 5, pp. 1513-1523.
Maxwell, Ian H., et. al., "A DNA cassette containing a trimerized SV40 polyadenylation signal which efficiently blocks spurious plasmid-initiated transcription", BioTechniques, 1989, vol. 7(3), pp. 276-280.
Meyers, Erik N., et al., "An Fgf8 mutant allelic series generated by Cre and Flp-mediated recombination", Nature Genetics, Feb. 1998, vol. 18, pp. 136-141.
Niwa, Hitoshi, et al., "Efficient selection for high-expression transfectants with a novel eukaryotic vector", Gene, 1991, vol. 108, pp. 193-200.

Okabe, Masaru, et al., "'Green mice' as a source of ubiquitous green cells", FEBS Letters, 1997, vol. 407, pp. 313-319.
Ordway, Jared M., et al., "Ectopically expressed CAG repeats cause intranuclear inclusions and a progressive late onset neurological phenotype in the mouse", Cell, Dec. 12, 1997, vol. 91, pp. 753-763.
Robberson, Barbara L., et al., "Exon definition may facilitate splice site selection in RNAs with multiple exons", Molecular and Cellular Biology, Jan. 1990, vol. 10, No. 1, pp. 84-94.
Soriano, Philippe., "Generalized lacZ expression with the ROSA26 Cre reporter strain", Nature Genetics, Jan. 1999, vol. 21, pp. 70-71.
Thomas, Kirk R., et al., "Site-directed mutagenesis by gene targeting in mouse embryo-derived stem cells", Cell, Nov. 6, 1987, vol. 51, pp. 503-512.
Zhang, Zuwen, et al., "Cre recombinase-mediated inversion using lox 66 and lox 71: method to introduce conditional point mutations into the CREB-binding protein", Nucleic Acids Research, 2002, vol. 30, No. 17, e90, pp. 1-5.
G. Roger Askew, "Evaluation of a conditional knockout gene trapping strategy", Power Point presentation presented at the $2^{nd}$ International Gene-Trap Workshop, in Frankfurt, Germany, on Jun. 1, 2002.
Lai et al., "Production of Alpha-1,3-Galactosyltransferase Knockout Pigs by Nuclear Transfer Cloning," Science 295:1089-92 (2002).
Supplementary Information for Lai et al. Report, Science Express, 4 pages (Jan. 3, 2002).
McCreath et al., "Production of gene-targeted sheep by nuclear transfer from cultured somatic cells," Nature 405:1066-69 (2000).
McCreath et al., "Production of gene-targeted sheep by nuclear transfer from cultured somatic cells," Nature, erratum, 1 page (2000).
Phelps et al., "Production of Alpha 1,3-Galactosyltransferase-Deficient Pigs," Science, 299:411-14 (2003).
Phelps, C.J., "Supporting Online Material" Science, 7 pages (Dec. 20, 2002).
Wang and Zhou, "Review: Specific genetic modifications of domestic animals by gene targeting and animal cloning," Reproductive Biology and Endocrinology 1:103 (2003).

* cited by examiner

Primary Examiner—Christopher S. F. Low
Assistant Examiner—Michele K. Joike
(74) Attorney, Agent, or Firm—Fitzpatrick, Cella, Harper & Scinto

(57) ABSTRACT

A method for conditionally knocking out and altering gene function and genetic sequences that can be used in such methods, for use in gene trapping and gene targeting. Specifically, the genetic sequence is a inducible gene silencer comprising: (a) a splice acceptor sequence; (b) an internal ribosomal entry site (IRES) sequence; (c) a nucleotide sequence coding for a reporter protein; (d) a polyadenylation sequence; and (e) a pair of oppositely oriented recombination site sequences, which cause single cycle inversions in the presence of a suitable recombinase enzyme, flanking elements (a) through (d).

16 Claims, 24 Drawing Sheets

Lox SITE MUTATION CLASSES AND SEQUENCES (SEQ ID NOS: 9-14)

▲ Lox P (SEQ ID NO: 9)    ATAACTTCGTATA   ATGTATGC   TATACGAAGTTAT

COMPATIBILITY MUTATIONS

△ L1 (SEQ ID NO: 10)    ATAACTTCGTATA   ATGTATAC   TATACGAAGTTAT

▲ L5171 (SEQ ID NO: 11)    ATAACTTCGTATA   ATGTGTAC   TATACGAAGTTAT

▲ L2272 (SEQ ID NO: 12)    ATAACTTCGTATA   AAGTATCC   TATACGAAGTTAT

TERMINATION MUTATIONS

△* L71 (SEQ ID NO: 13)    ATAACTTCGTATA   ATGTATGC   TATACGAACGGTA

▲* L66 (SEQ ID NO: 14)    TACCGTTCGTATA   ATGTATGC   TATACGAAGTTAT

*FIG. 5*

AN INDUCIBLE GENE SILENCER

SA: ADENOVIRUS MAJOR LATE TRANSCRIPT

STOP: gtcTGAcTAAcTAGcTAGcTAAgTGAgaagaagaaaagctt

IRES: 5' UTR OF Gtx HOMEODOMAIN PROTEIN

PolyA: 4X SV40 Poly A

FUNCTIONAL TESTING OF THE INDUCIBLE GENE SILENCER: EXPRESSION ANALYSIS
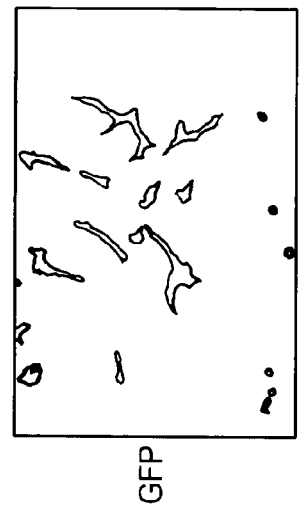
FIG.11A CONTROL PLASMID GFP
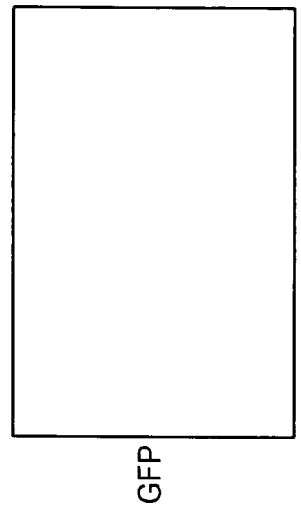
FIG.11C PCX-IGSInert-RFP GFP
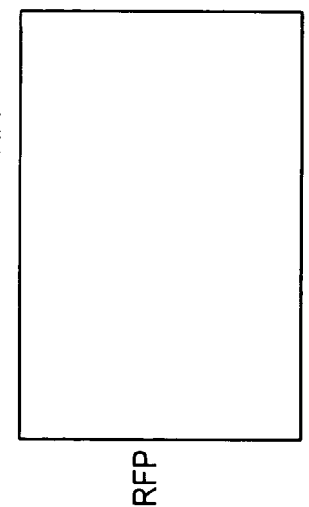
FIG.11E PCX-IGSKO-RFP GFP
FIG.11B CONTROL PLASMID RFP
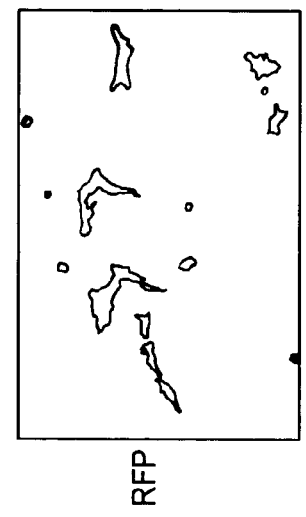
FIG.11D PCX-IGSInert-RFP RFP
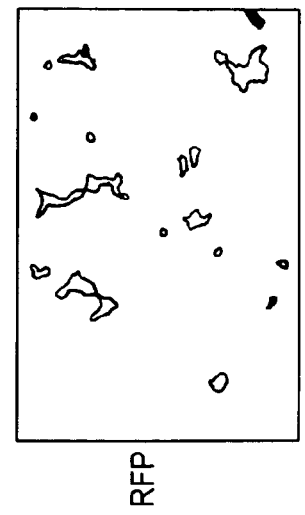
FIG.11F PCX-IGSKO-RFP RFP

DNA SEQUENCE AND ELEMENTS OF AN INDUCIBLE GENE SILENCER
(SEQ ID NO: 1)

```
AAAACGACGGCCAGTGAATTGTAATACGACTCACTATAGGGCGAATTGGG

CCCGACGTCGCATGCTCCCGGCCGCCATGGCGGCCGCGGGAATTCGATTA

AGGCGCCGCTAGCGGATCCATAACTTCGTATAATGTATGCTATACGAACG
                <-------Lox71-(SEQ ID NO: 2)---
GTAATCTGTAGGGCGCAGTAGTCCAGGGTTTCCTTGATGATGTCATACTT
--><-----------------------------------------------
ATCCTGTCCCTTTTTTTTCCACAGCTCGCGGTTGAGGACAAACTCTTCGC
------------------Splice Acceptor-(SEQ ID NO: 3)--
GGTCTTTCCAGTGGGGATCGACGGTATCTGCAGGTCTGACTAACTAGCTA
------------------------------><-All Frame Stop--
GCTAAGTGAGCAGGCGGCCGCGAATTCTTCTGACATCCGGCGGGTTTCTG
--(SEQ ID NO: 4)----><-----------------------------
ACATCCGGCGGGTTTCTGACATCCGGCGGGTTTCTGACATCCGGCGGGTT
-GTX-IRES-(SEQ ID NO: 5)---------------------------
TCTGACATCCGGCGGGTGACTCACAACCCCAGAAACAGACATCCATGGCG
-----------------------------------------------><---
GCCGGGAGCAATGCACTGCAGATGCAGCTGCAGGAATTCGCCACCATGGT
---------------------------------------------------
GAGCAAGGGCGAGGAGCTGTTCACCGGGGTGGTGCCCATCCTGGTCGAGC
---------------------------------------------------
TGGACGGCGACGTAAACGGCCACAAGTTCAGCGTGTCCGGCGAGGGCGAG
---------------------------------------------------
```

FIG. 12A

DNA SEQUENCE AND ELEMENTS OF AN INDUCIBLE GENE SILENCER
(SEQ ID NO: 1) (CONTINUED)

```
GGCGATGCCACCTACGGCAAGCTGACCCTGAAGTTCATCTGCACCACCGG
--------------------------------------------------

CAAGCTGCCCGTGCCCTGGCCCACCCTCGTGACCACCCTGACCTACGGCG
--------------------------------------------------

TGCAGTGCTTCAGCCGCTACCCCGACCACATGAAGCAGCACGACTTCTTC
---------------------------EGFP-(SEQ ID NO: 6)-

AAGTCCGCCATGCCCGAAGGCTACGTCCAGGAGCGCACCATCTTCTTCAA
--------------------------------------------------

GGACGACGGCAACTACAAGACCCGCGCCGAGGTGAAGTTCGAGGGCGACA
--------------------------------------------------

CCCTGGTGAACCGCATCGAGCTGAAGGGCATCGACTTCAAGGAGGACGGC
--------------------------------------------------

AACATCCTGGGGCACAAGCTGGAGTACAACTACAACAGCCACAACGTCTA
--------------------------------------------------

TATCATGGCCGACAAGCAGAAGAACGGCATCAAGGTGAACTTCAAGATCC
--------------------------------------------------

GCCACAACATCGAGGACGGCAGCGTGCAGCTCGCCGACCACTACCAGCAG
--------------------------------------------------

AACACCCCCATCGGCGACGGCCCCGTGCTGCTGCCCGACAACCACTACCT
--------------------------------------------------

GAGCACCCAGTCCGCCCTGAGCAAAGACCCCAACGAGAAGCGCGATCACA
--------------------------------------------------

TGGTCCTGCTGGAGTTCGTGACCGCCGCGGGATCACTCTCGGCATGGAC
-------------------------------------------------->
```

FIG. 12B

DNA SEQUENCE AND ELEMENTS OF AN INDUCIBLE GENE SILENCER
(SEQ ID NO: 1) (CONTINUED)

```
GAGCTGTACAAGTAAGAATTCGATATCAAGCTTGCAGATCTGCGACTCTA
<------------------------4X-PolyA-(SEQ ID NO: 7)-
GAGGATCTGCGACTCTAGAGGATCATAATCAGCCATACCACATTTGTAGA
--------------------------------------------------

GGTTTTACTTGCTTTAAAAACCTCCCACACCTCCCCCTGAACCTGAAAC
-------------------------------------------------

ATAAAATGAATGCAATTGTTGTTGTTAACTTGTTTATTGCAGCTTATAAT
--------------------------------------------------

GGTTACAAATAAAGCAATAGCATCACAAATTTCACAAATAAAGCATTTTT
--------------------------------------------------

TTCACTGCATTCTAGTTGTGGTTTGTCCAAACTCATCAATGTATCTTATC
--------------------------------------------------

ATGTCTGGATCTGCGACTCTAGAGGATCATAATCAGCCATACCACATTTG
--------------------------------------------------

TAGAGGTTTTACTTGCTTTAAAAACCTCCCACACCTCCCCCTGAACCTG
-------------------------------------------------

AAACATAAAATGAATGCAATTGTTGTTGTTAACTTGTTTATTGCAGCTTA
--------------------------------------------------

TAATGGTTACAAATAAAGCAATAGCATCACAAATTTCACAAATAAAGCAT
--------------------------------------------------

TTTTTTCACTGCATTCTAGTTGTGGTTTGTCCAAACTCATCAATGTATCT
--------------------------------------------------

TATCATGTCTGGATCTGCGACTCTAGAGGATCATAATCAGCCATACCACA
--------------------------------------------------
```

FIG. 12C

DNA SEQUENCE AND ELEMENTS OF AN INDUCIBLE GENE SILENCER
(SEQ ID NO: 1) (CONTINUED)

```
TTTGTAGAGGTTTTACTTGCTTTAAAAAACCTCCCACACCTCCCCCTGAA
--------------------------------------------------

CCTGAAACATAAAATGAATGCAATTGTTGTTGTTAACTTGTTTATTGCAG
--------------------------------------------------

CTTATAATGGTTACAAATAAAGCAATAGCATCACAAATTTCACAAATAAA
--------------------------------------------------

GCATTTTTTTCACTGCATTCTAGTTGTGGTTTGTCCAAACTCATCAATGT
--------------------------------------------------

ATCTTATCATGTCTGGATAACTTCGTATAGCATACATTATACGAACGGTA
---------------><--Lox66-(SEQ ID NO: 8)---------->

GGATCCACGCGTGCTAGCAATTCGATATCACTAGTGAATTCGCGGCCGCC

TGCATAGCTTGAGTATTCTATAGTGTCACCTAA
```

FIG. 12D

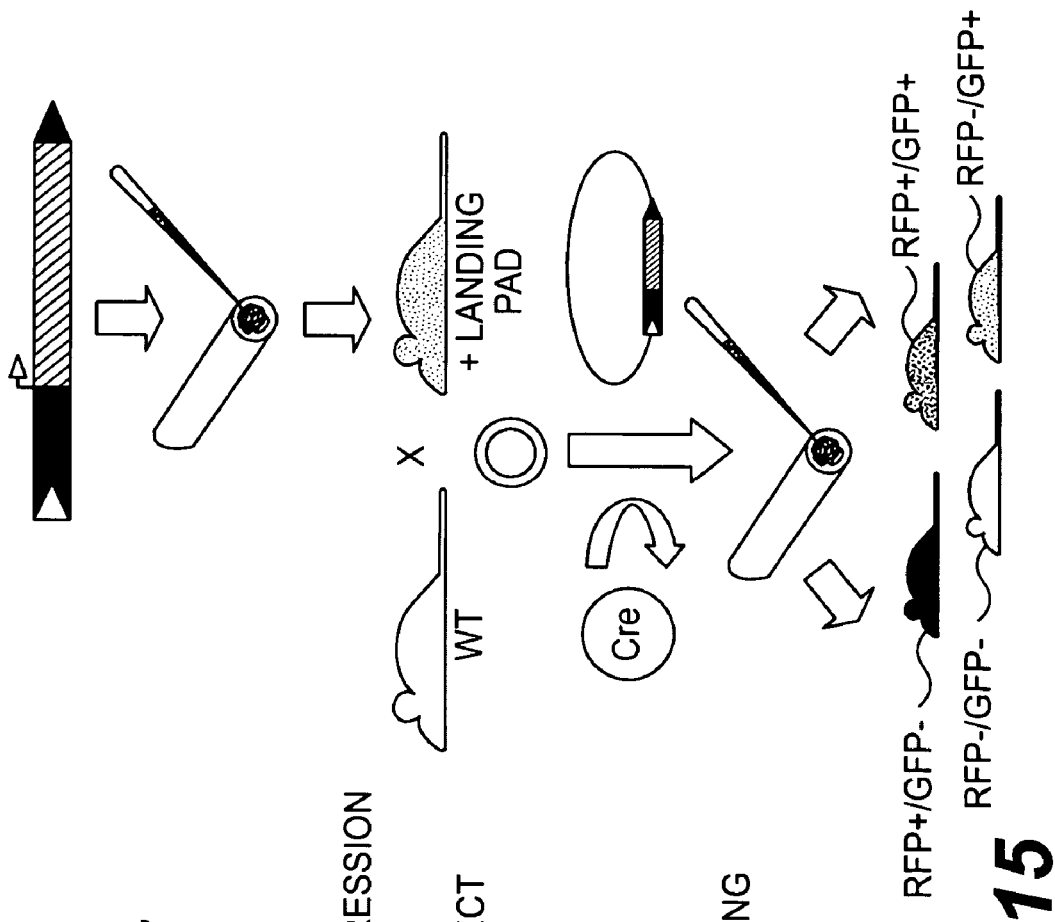

INVERSION OF THE IGS IN TARGETED ES CELLS

SOUTHERN BLOT ANALYSIS FOR HPRT-IGS GENE TARGETED ES CELLS wt  G10

8.2 kb
6.0 kb

CONDITIONAL KNOCKOUT METHOD FOR GENE TRAPPING AND GENE TARGETING USING AN INDUCIBLE GENE SILENCER

FIELD OF THE INVENTION

This invention relates to a method of gene manipulation. In particular, this invention relates to a method for conditionally knocking out or altering gene function. The invention also relates to genetic sequences that can be used in such methods, and for use in gene trapping and gene targeting activities.

BACKGROUND OF THE INVENTION

Being able to control and manipulate gene function and gene expression forms the basis of recombinant DNA engineering. For example, over time, various methods have been developed for knocking out gene expression. By knocking out a gene's activity, it is possible to study its function.

Traditionally, a direct gene disruption method (i.e., also later referred to as "the conventional knockout method") was used to knock out a gene. This involved inserting a DNA fragment containing a desired mutant gene (or part of a gene) into a vector and then introducing the vector into, for example, embryo-derived mouse stem cells (i.e., embryonic stem cells or ES cells). The DNA fragment could include, for example, a neomycin selectable marker. Most insertions would occur in random sites in the mouse genome. So long as the fragment introduced itself into an exon upon introduction into an ES cell, the fragment would disrupt the expression of the gene of which the exon is a part. However, by this method, there was no control over when a gene might be knocked out. Also, if a gene were developmentally required, even if for a role that was different than the one that a scientist was interested in studying, then there was nothing that the scientist could do —the gene could end up causing developmental lethality, thus making it impossible to further pursue a study of the gene's later role.

The conditional knockout method based on recombinase mediated deletion was an improvement over the conventional knockout method. Using the conditional knockout method, a scientist would introduce, for example, Lox sites (i.e., short for "locus of crossover" sites) into the introns of a gene that is to be disrupted. Lox sites are DNA sequences that, when found in a pair in the same orientation in a length of DNA, function to remove any intervening DNA sequence found between the two LoxP sites when in the presence of Cre recombinase (i.e., or "Cre"), a 38 kD site-specific recombinase. (Cre is short for causes recombination.) As shown in FIG. 1, using a conditional knockout strategy, since the LoxP sites are to be inserted into the introns of genes, they remain inert, in theory, and do not affect the mature transcript that ends up being translated into a protein when Cre is absent. This made the knocking out of the gene into which the Lox sites have been inserted conditional upon the delivery of Cre to the cell. Cre could then be delivered using a vector, such as a viral vector.

The deletion-based conditional knockout method is illustrated in FIG. 1. In FIG. 1, the first allele shows two Lox sites as triangular elements in the same orientation inserted in two intron sequences of a gene that has three exons. The Lox sites flank two exons. The arrow at the first exon shows where transcription starts for the gene. In the absence of Cre, the gene in the first allele (i.e., all its exons) should get transcribed and translated normally. However, upon the addition of Cre, recombination between LoxP sites causes the second and third exons to be removed, as shown in the second allele. As a result, the gene in the second allele is disrupted, i.e., knocked out.

Deletion-based conditional knockout animal models are advantageous over direct gene disruption animal models in that the former avoids developmental lethality. For example, if a gene is initially important for liver development in an organism but later is expressed in the organism's heart tissue, and it is the gene's expression in heart tissue that a scientist wishes to study, the scientist can use a conditional knockout strategy to keep the gene intact during development, and then to disrupt the gene in heart tissue upon specific delivery of Cre to that tissue. This phenomenon also leads to greater control and flexibility in experimentation, since one can conduct a temporal and/or tissue specific knockout based on the mechanism of Cre delivery.

However, a disadvantage of the deletion-based conditional knockout strategy involving the Cre/LoxP system is that the scientist must know a great deal about the gene under study, including its essential domains, so as to be able to properly insert the Lox sites. If the Lox sites end up disrupting an exon, they will not be inert. Also, it is important that the Lox sites flank important parts of a gene that are critical to gene function. Moreover, the scientist must be aware of all the different transcripts that might be encoded by the same gene. As well, when genes are very large or have multiple essential exons that are far apart from one another, it may be very difficult to engineer a conditional knockout mutant gene. Thus the construct design and preparation for conditional knockout experiments are more complicated than in conventional knockout by gene disruption experiments.

Yet another method exists for knocking out genes called gene trapping, as shown in FIG. 2. The gene trap method provides an approach for creating random gene knockouts in cells and animals as opposed to the gene specific approach of gene targeted knockouts provided, for example, by the two methods described above. The first allele shown on FIG. 2 is a wild-type gene with three exons, and has a transcription start site at the arrow. The second allele in FIG. 2 illustrates a gene trap, a single genetic construct that is introduced into an intron. The gene trap would also function if it were inserted into an exon. For example, the gene trap shown in FIG. 2 contains a splice acceptor ("SA") that forces splicing from any exon to itself during transcription, a reporter gene (i.e., LacZ) that, because of the SA, will get transcribed as a hybrid message with the initial portion of the wild-type gene, and a neomycin resistance gene which is used to select any cells that might have incorporated the gene trap into its genome. Gene traps cause random gene disruption since they are inserted randomly into the genome. As a result, they can be used for the in vitro identification and discovery of new genes. In this regard, the gene trap provides a genetic tag that can be used to identify the trapped gene. However, gene trapping does not provide much experimental control and does not allow a scientist, for example, to track a particular gene from development and then disrupt the specific gene at a particular point in time.

Therefore, in summary, the conventional knockout method involves a simple construction and is gene specific, the deletion-based conditional knockout method involves a complex construction and is gene specific, and the gene trapping knockout method is simple and random.

SUMMARY OF THE INVENTION

Accordingly, there is a need for a recombinant DNA technique that allows a scientist to control the knockout of a specific gene at a specific point in time by way of an experimental technique that involves less genetic manipulation and yet provides a predictable reporter transcript, and utilizes a genetic construct that can be prepared and inserted into a target gene more efficiently than in the past. We have developed just such a technique using a novel genetic construct. Our method involves both a simple construction and can be used in either a random or gene specific manner.

In one aspect, our invention provides an inducible gene silencer comprising: a splice acceptor sequence; an internal ribosomal entry site (IRES) sequence; a nucleotide sequence coding for a reporter protein; a polyadenylation sequence; and a pair of oppositely oriented recombination site sequences, which cause single cycle inversions in the presence of a suitable recombinase enzyme, flanking the previously-noted elements.

More specifically, our invention provides an inducible gene silencer, as set forth in SEQ ID NO: 1.

Another aspect of our invention provides an inducible gene silencer comprising nucleotide sequences coding for: a splice acceptor, a reporter protein, and a selection marker, flanked by a pair of recombination site sequences which cause single inversion in the presence of a suitable recombinase enzyme.

In still another alternative embodiment, this invention provides a eukaryotic gene comprising, within its introns, a first inducible gene silencer, which is exogenous to the gene, the inducible gene silencer comprising: a splice acceptor sequence; an internal ribosomal entry site (IRES) sequence; a nucleotide sequence coding for a reporter protein; a polyadenylation sequence; and a pair of oppositely oriented Lox sites with termination mutations in opposing arms flanking the previously identified elements; in combination with one or more exogenous elements selected from the group consisting of: (a) a second inducible gene silencer comprising: a splice acceptor and a selection marker or a reporter protein, flanked by Frt sites; (b) a Lox site containing a core mutation; and (c) a pair of Lox sites, each placed in the same orientation within different introns, such that the pair of Lox sites flanks one or more exons.

Our invention also provides a conditional knockout gene trapping or gene targeting method comprising the steps of preparing an inducible gene silencer comprising: a splice acceptor sequence; an internal ribosomal entry site (IRES) sequence; a nucleotide sequence coding for a reporter protein; a polyadenylation sequence; and a pair of oppositely oriented recombination site sequences which cause single cycle inversions in the presence of a suitable recombinase enzyme, flanking the previously identified elements; inserting the inducible gene silencer into a vector in an inert orientation; transfecting the vector comprising the inducible gene silencer into a host cell; delivering a suitable recombinase enzyme to the host cell or to any organism deriving from the host cell, at any desired time, to cause the inducible gene silencer to invert into an active orientation, such that the inducible gene silencer knocks out the functioning of a gene into which it has inserted, and expresses the reporter protein.

In yet another aspect, our invention provides a method of knocking out the expression of a gene of interest at a future point in time, comprising the steps of: preparing an inducible gene silencer comprising: a splice acceptor sequence; an internal ribosomal entry site (IRES) sequence; a nucleotide sequence coding or a reporter protein; a polyadenylation sequence; and a pair of oppositely oriented recombination site sequences which cause single cycle inversions in the presence of a suitable recombinase enzyme, flanking the previously identified elements; inserting the inducible gene silencer into an intron of the gene of interest in an inert orientation; and exposing the gene of interest containing the inducible gene silencer to a recombinase enzyme at the future point in time, such that the inducible gene silencer inverts to an active orientation, thereby causing the gene of interest to cease normal expression.

BRIEF DESCRIPTION OF THE DRAWINGS

FIG. 5 provides genetic sequences for a wild-type LoxP site and mutant Lox sequences having compatibility or termination mutations.

FIGS. 11A to 11F show further results of the functional testing of the inducible gene silencer of FIGS. 12A to 12D.

FIGS. 12A to 12D show a DNA sequence and the elements of a most preferred inducible gene silencer.

FIG. 15 shows the steps in a site-directed transgenics experiment involving a Cre recombinase mediated cassette exchange.

DETAILED DESCRIPTION OF THE INVENTION

We have developed a new recombinant DNA technique by which we can control the knockout of a specific gene at a specific point in time that involves less genetic manipulation than in prior techniques, and yet provides a predictable reporter transcript. Moreover, this new recombinant DNA technique utilizes a genetic construct that can be prepared and inserted into a target gene more efficiently than in the past. This is a new conditional knockout technique that can be used for gene trapping or gene targeting.

Figure 3A:
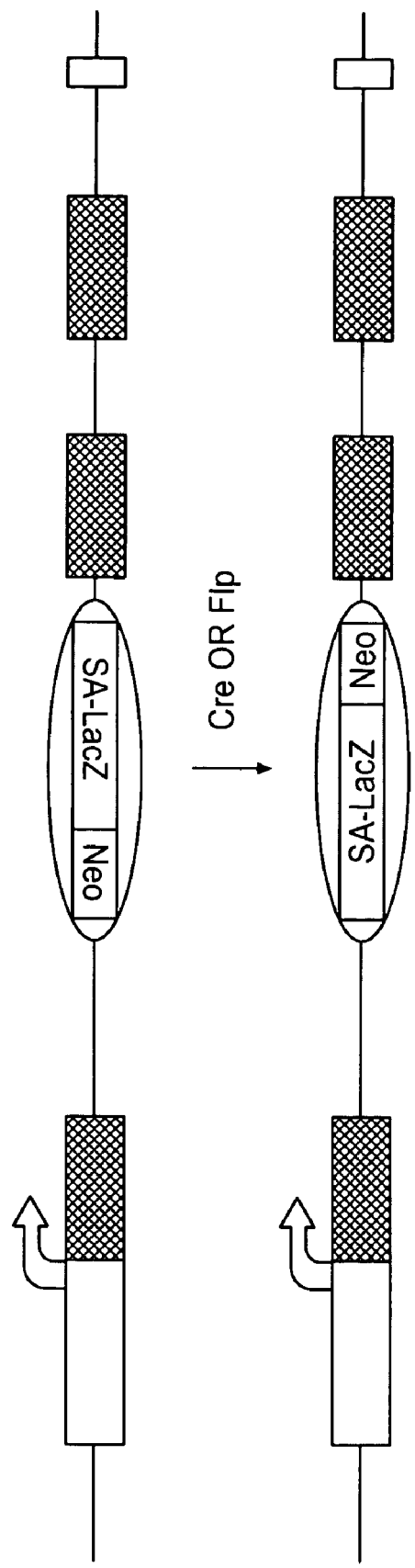
FIG. 3A shows the basic concept behind a conditional knockout gene trapping or gene targeting strategy, namely, an inducible gene silencer.
Figure 3B:
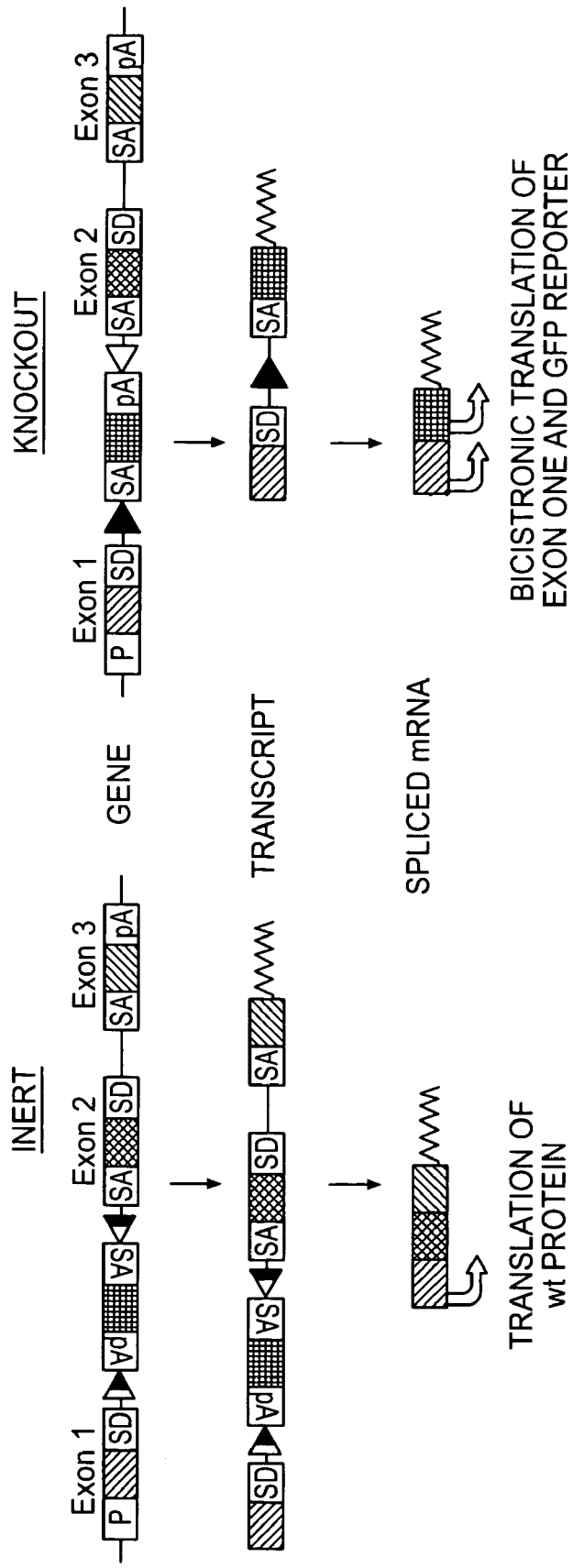
FIG. 3B shows inert and knockout splicing products resulting from the use of an inducible gene silencer.

FIG. 3A shows a genetic construct for use in our invention, namely, a basic inducible gene silencer. The first allele shown in FIG. 3A illustrates a gene having three endogenous exons, depicted as shaded rectangles, with a transcriptional start site within the first exon. The basic inducible gene silencer is inserted into the intron between the first and second endogenous exons in an inert orientation, i.e., backwards. By introducing this one genetic construct in an intron, and in an inert orientation, no disruption of the gene's activity occurs. As shown in FIG. 3A, the genetic construct contains a neomycin resistance gene that has its own promoter and is active in either the forward or backward direction. Thus, it can be used as a selection marker to identify cells that contain the construct. Moreover, the genetic construct contains a splice acceptor (i.e., "SA"), followed by the LacZ gene. Also, although not shown, the genetic construct also must contain a pair of recombination site sequences (e.g., mutant Lox or Frt sites) which cause single cycle inversion in the presence of a suitable recombinase enzyme. For example, when Cre or Flp recombinase is added to a system containing the first allele shown in FIG. 3A, the genetic construct will invert into the knockout orientation illustrated by the second allele and cause gene function to be disrupted. The technique described generally in FIG. 3A is advantageous over prior techniques since it is easier in that it is not necessary to insert two Lox sites in different locations within a gene, and it is not necessary to know structural details of the gene including essential exons of the gene. FIG. 3B shows schematically how a gene with three exons will eventually get spliced into mRNA if the gene contains an inducible gene silencer in the inert orientation or the active orientation. In the former case, all three exons will get spliced to generate a normal mRNA. In the latter case, the spliced mRNA will contain a bicistronic translation of the first exon and a reporter gene, such as the gene for green fluorescent protein (GFP).

Figure 4A:
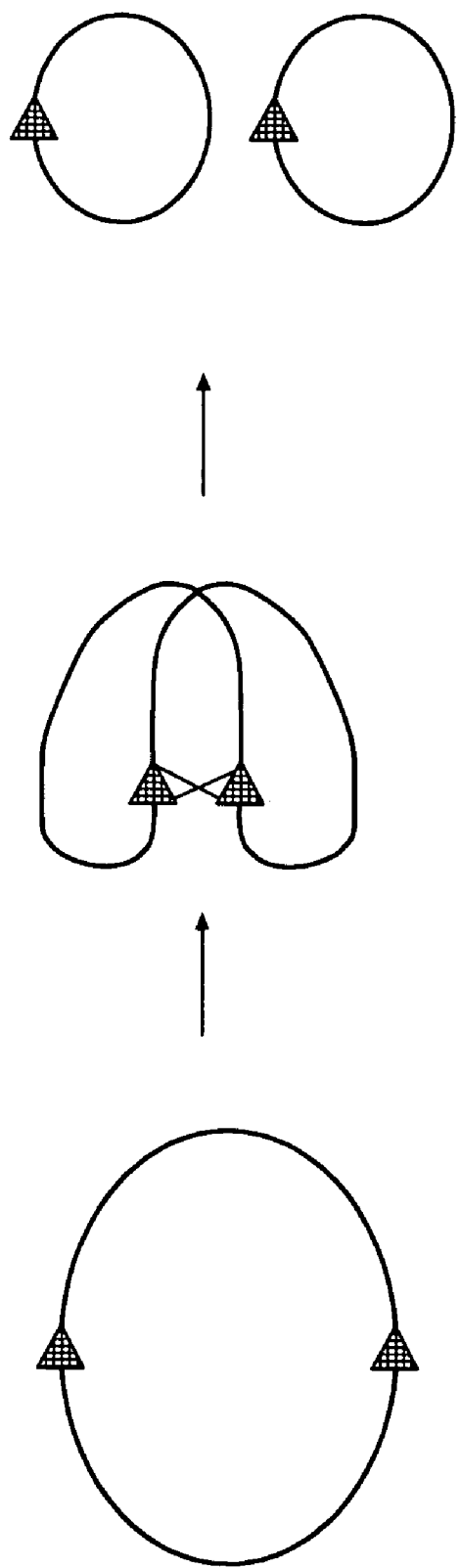
FIG. 4A shows an example of Cre-mediated recombination, specifically, the mechanism of a deletion involving Lox sites.

To better understand the preferred embodiment of our invention, it is necessary to understand how Cre-mediated recombination works, both using wild type Lox P and mutated Lox sites. Cre recombinase is a 38 kD protein that causes recombination of DNA at "locus of crossing over" or Lox sites, which are 34 bp DNA target sites. FIG. 4A shows a schematic of the mechanism by which Cre recombinase causes a circular piece of DNA to cross over and then delete a portion of the DNA, so as to result in two separate circular pieces of DNA, each containing a Lox site. The characteristic sequence of a Lox site has palindromic 13 bp left and right arm sequences flanking an 8 bp core of unique sequence, as seen in FIG. 5.

Figure 4B:
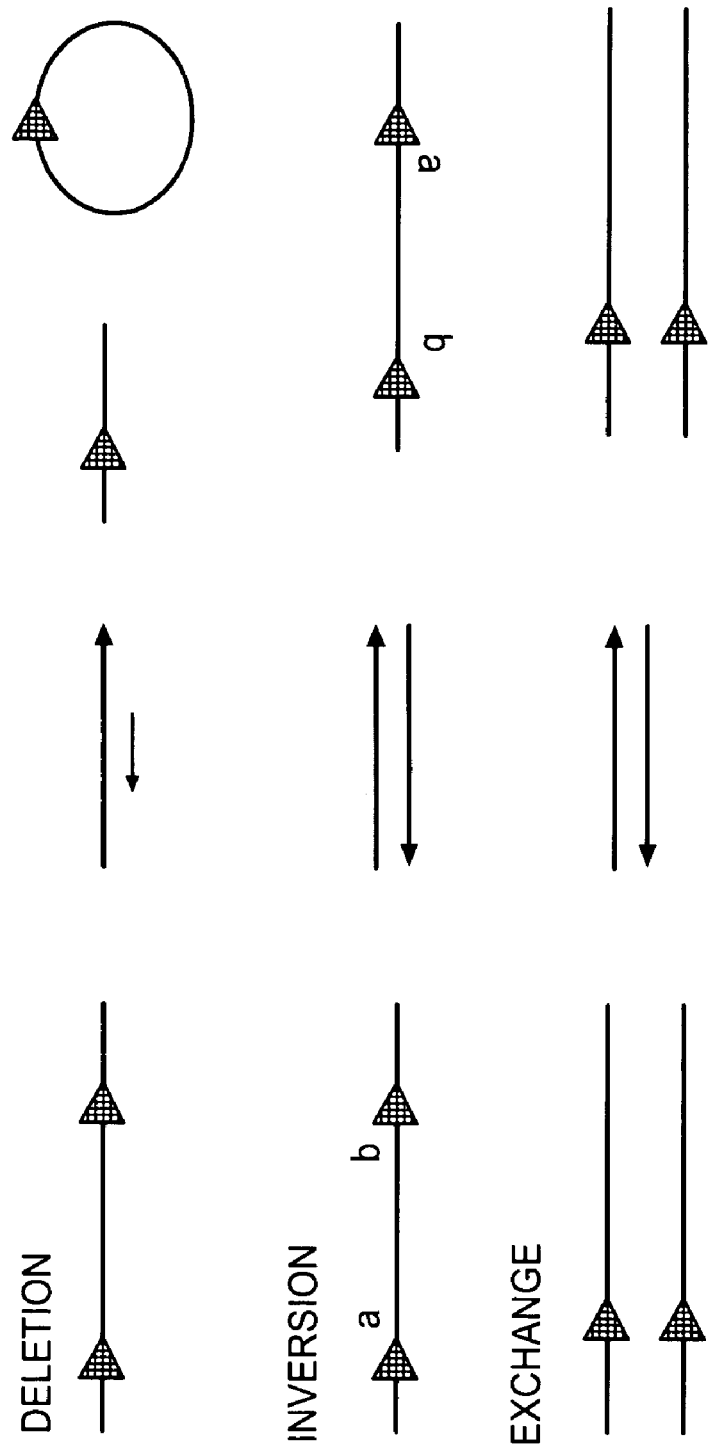
FIG. 4B shows various examples of Cre-mediated recombination events, namely, a deletion, an inversion, and an exchange, all involving wild-type LoxP sites.

FIG. 4B shows various examples of Cre-mediated recombination events, namely, a deletion, an inversion, and an exchange, all involving wild-type Lox sites. The deletion of DNA between two Lox sites occurs, as shown in FIG. 4B, when the Lox sites exist in the same orientation in the DNA sequence. In this situation, the reaction sequence highly favors the deletion of a portion of DNA between the Lox sites, which will diffuse away from the main piece of DNA as a circular piece of DNA. On the other hand, if Lox sites are inserted into a piece of DNA such as to be in opposing orientations, Cre recombinase will cause the intervening piece of DNA to flip back and forth between the sites, in a reaction equilibrium. Finally, Cre recombinase can also act to exchange one piece of DNA for another when two DNA sequences are brought into sufficiently close proximity, and each contains a Lox site, wherein both Lox sites are in the same orientation. However, no one direction of this exchange reaction is favored.

Figure 6:
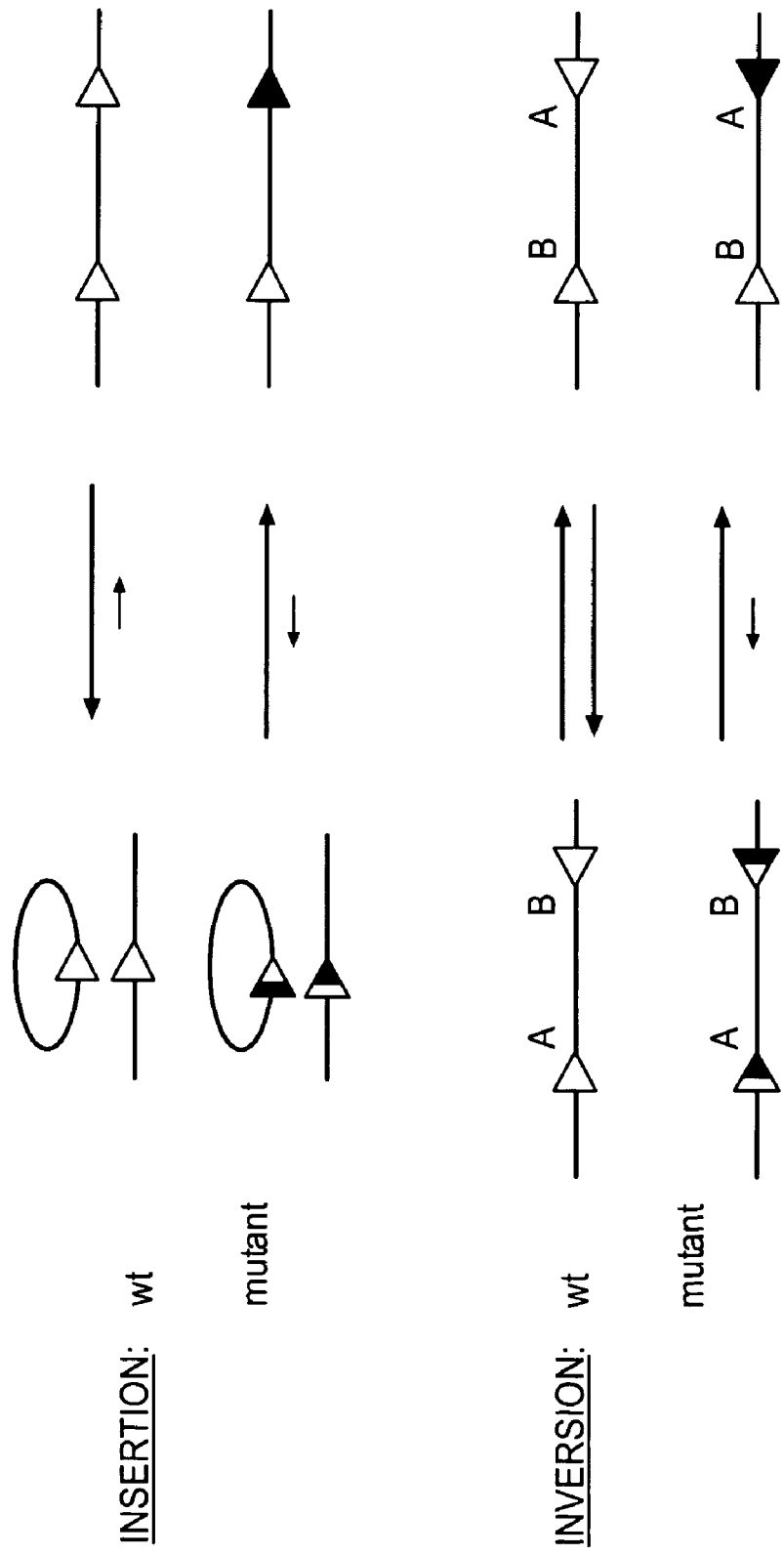
FIG. 6 shows single cycle (dead end) substrates resulting from insertion and inversion reactions involving mutant LoxP sites, as compared to such reactions involving wild-type LoxP sites.

As noted earlier, FIGS. 4A and 4B show the activity of Cre-recombinase on wild-type Lox sites. However, mutations can be introduced into Lox sites to alter this wild-type activity. For example, as shown in FIG. 5, compatibility mutations can be introduced by introducing mutations in the core sequence of a Lox site (i.e., L5171 (a.k.a. Lox C) or L2272 (a.k.a. Lox D)). As will be discussed further later, in the context of FIGS. 16A and 16B, when two different Lox sites, having at least one but preferably two nucleotide compatability substitutions, are in close proximity, recombinase mediated cassette exchange can occur. As well, Lox sites can be altered from wild type, by having termination mutations introduced into either the left arm or the right arm of the Lox site DNA sequence. In particular, FIG. 5 shows a Lox site DNA sequence known as L71, which has a mutation in the right arm, and a Lox site DNA sequence known as L66, which has a mutation in the left arm. For example, by using a pair of Lox sites having reciprocal termination mutations, the Cre-mediated insertion reaction is favored over the deletion reaction, as shown in FIG. 6. Further explanation as to how this occurs is provided in the context of our discussion of FIG. 6. Each of the Lox sequences shown in FIG. 5 is also provided in the attached sequence listing and is identified as follows: LoxP (SEQ ID NO:. 9), L1(SEQ ID NO:. 10), L5171 (a.k.a. LoxC) (SEQ ID NO:. 11), L2272 (a.k.a. LoxD) (SEQ ID NO:. 12), L71 (a.k.a. Lox71) (SEQ ID NO:. 13), and L66 (a.k.a. Lox66) (SEQ ID NO:. 14).

FIG. 6 shows single cycle (dead end substrates) that result from insertion and inversion reactions involving termination mutant Lox sites, as compared to such reactions involving wild-type Lox sites. More specifically, a circular piece of DNA that contains a Lox site having a right arm termination mutation that is in close proximity to a second strand of DNA containing a mutant Lox site, having a termination mutation in the left arm, leads to a forward-favored reaction, wherein two things occur. First, the circular piece of DNA inserts into the other DNA sequence. Second, the mutations, in the Lox sites accumulate in one of the sites, such that one Lox site contains double mutations, and the other Lox site become wild type. This leads to only a single cycle recombination reaction and a dead end substrate, namely, the piece of DNA with the circular DNA inserted therein. In the wild-type scenario, the reaction kinetics are such that such an insertion would not tend to occur in a stable manner.

Similar rearrangements of the mutant Lox sites occur with inversion-type reactions. As discussed earlier, in the wild type situation, wild type Lox sites that are in opposing orientation to one another will be in a constant equilibrium of having DNA flipping back and forth between the two sites. On the other hand, when two mutant Lox sites are inserted in opposing orientation, where one Lox site has a left arm termination mutation, and the other Lox site has a right arm termination mutation, then the forward reaction will be favored, and a single cycle of the reaction will occur, wherein the intervening piece of DNA between the Lox sites will be flipped once into the opposite orientation from which it was originally placed. The termination mutations are such that they reduce the affinity of Cre recombinase for the Lox site. When a mutation exists only in one or the other arms of the Lox site DNA sequence, the affinity of Cre recombinase for the Lox site will be reduced, but the site will be active. However, this affinity is further reduced for Lox sites having accumulated left and right arm termination mutations, such that these double mutant Lox sites are functionally inactive. It is for this reason that the reaction sequence only occurs once, as shown with the insertion and inversion schemes provided in FIG. 6.

Figure 2:
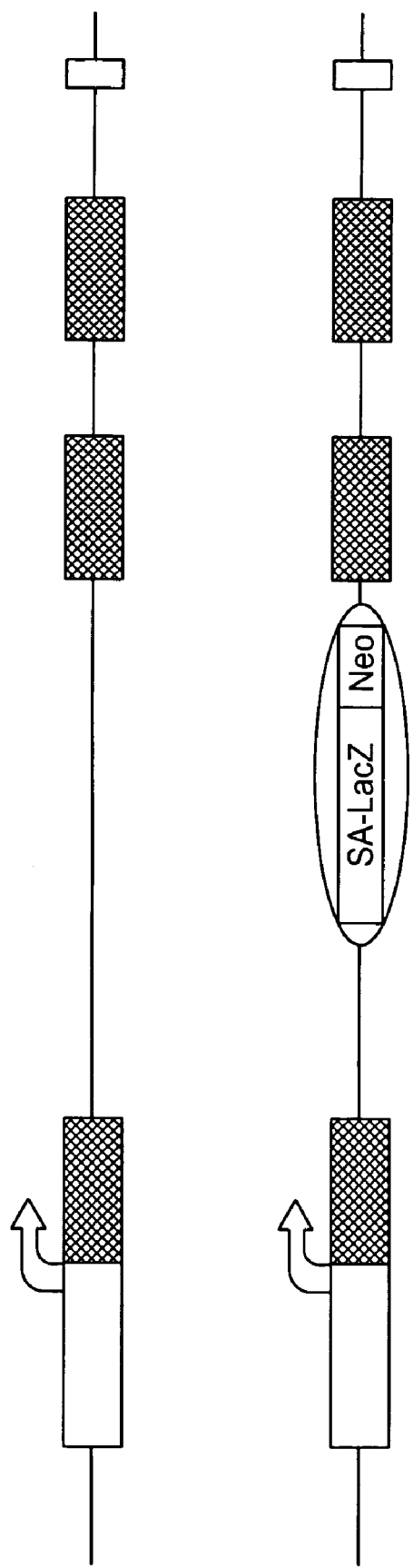
FIG. 2 shows one wild-type allele and one allele subjected to a conventional gene trapping strategy.

Further information regarding wild type and mutant Lox sites can be found, for example, in an article by Albert, et al., "Site-specific integration of DNA into wild-type and mutant Lox sites placed in the plant genome", The Plant Journal, 1995, volume 7(4), pages 649-659. See also Zhang, et al., "Cre recombinase-mediated inversion using Lox 66 and Lox 71: Method to introduce conditional point mutations into the CREB-binding protein", Nucleic Acids Research, 2002, volume 30, no. 17, e90, pages 1-5. We note that Zhang, et al., describe a method involving mutant Lox sites to introduce a point mutation in the mouse genome in a tissue- and time-specific manner. The Zhang, et al. approach is illustrated in FIG. 2 of their article. While Zhang, et al. provide a method by which to conditionally insert the point mutation, this is different from our method which causes conditional disruption of the gene and translation of a reporter protein, such as GFP.

Figure 7:
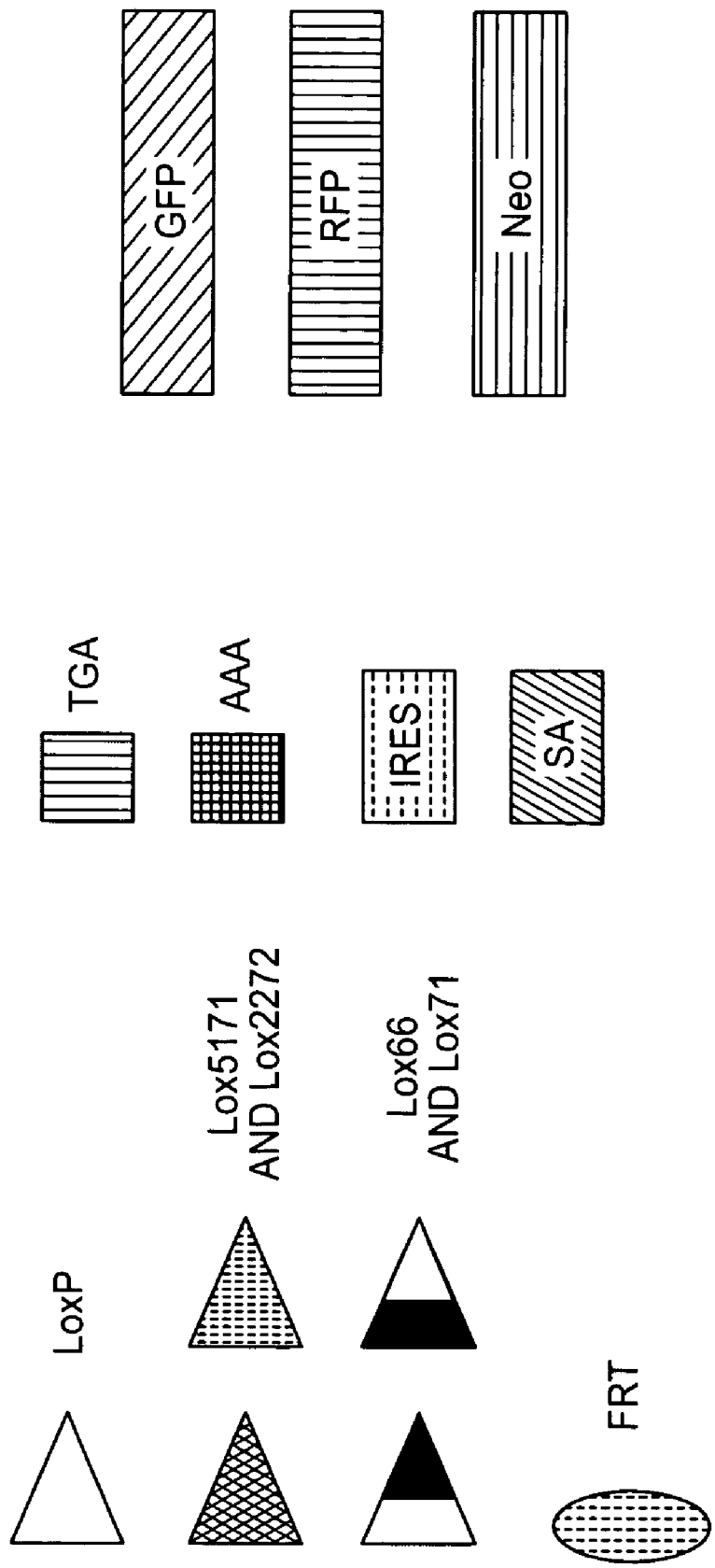
FIG. 7 shows various DNA elements for use in an inducible gene silencer.

FIG. 7 shows various DNA elements that we use in constructing our novel type of DNA sequence that can be used in our conditional knockout gene trapping and gene targeting strategy. For example, various triangular elements are shown in FIG. 6 which represent wild-type or mutated Lox sites. Mutant Lox sites, L5171 and L2272, as noted in FIG. 5, are Lox sites that contain core or compatibility mutations. In addition to Lox recombination sites, we show, in FIG. 7, an oval element representing a Frt site, namely, the recombination sequence that is specific to Flp recombinase. Frt sites work in essentially the same way as Lox sites. For example, in one embodiment of our invention, we envision using a pair of Frt sites to flank a selectable marker gene, for example the neomycin resistance gene. (The use of Flp recombinase in gene targeting is described in Meyers, E. N., et al., "An Fgf8 mutant allelic series generated by Cre- and Flp-mediated recombination", Nature Genetics, February 1998, vol. 18(2), pp. 136-41.)

FIG. 7, in addition to recombination sites, also shows various elements that are required for gene activity. The square element marked "TGA" represents an all-frame translational stop sequence, and the checkerboard square represents a polyadenylation sequence which functions as a transcriptional stop. Moreover, the rectangle marked "IRES" represents an "internal ribosomal entry site", which in the mature transcript provides a site, downstream of the endogenous translation start site, at which a ribosome can bind and initiate translation. The rectangular element marked "SA" represents a splice acceptor. This element forces splicing from the upstream exon to itself, i.e., it causes any endogenous gene to splice to the splice acceptor and any message that follows it, thereby creating a hybrid message.

Figure 8:
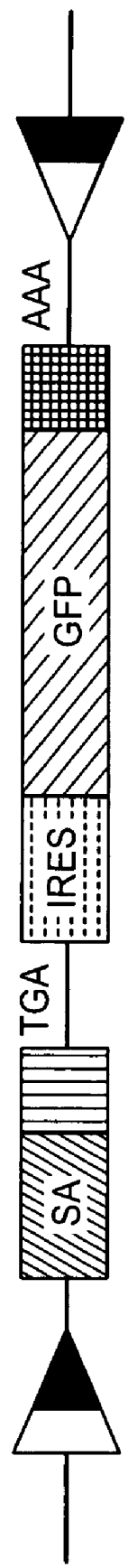
FIG. 8 shows the structure of an inducible gene silencer, including the identity of the various DNA elements included in the inducible gene silencer.

Finally, the third column of DNA elements shows various reporter or selection type gene sequences. For example, the rectangular element labeled as "GFP" represents the DNA sequence for green fluorescent protein, whereas the rectangular element labeled "RFP" represents the DNA sequence for red fluorescent protein. Furthermore, the rectangular element marked "Neo" is a selection marker by which we can identify cells containing a genetic construct by those which exhibit neomycin resistance. Additional details regarding these various elements will be provided in our discussion of an inducible gene silencer that can preferably be prepared for use in a conditional knockout experiment, as shown in FIG. 8. Additional information regarding GFP or green fluorescent protein, as well as our most preferred reporter protein, enhanced GFP (EGFP), can be found, for example, in an article by Okabe, et al., "'Green mice' as a source of ubiquitous green cells", FEBS Letters, 1997, volume 407, pages 313-319, the content of which is herein incorporated by reference.

As shown in FIG. 8, our preferred inducible gene silencer contains a number of elements between a pair of Lox sites having termination mutations in opposite arms of the Lox DNA sequence. Included between these Lox sites are DNA sequences for: a splice acceptor, a translational stop (i.e., the element marked as "TGA"), an IRES site, a GFP reporter; and a polyadenylation sequence. As suggested above, the splice acceptor forces splicing from an upstream exon to itself. Information regarding splice acceptors can be found in Friedrich, G. & Soriano, P., "Promoter traps in embryonic stem cells: a genetics screen to identify and mutate developmental genes in mice," Genes & Development, 1991, vol. 5(9), pp. 1513-1523. Although not critical to the operation of our new inducible gene silencer, the translational stop terminates translation of the fusion transcript. That is, if a mature fusion message of the endogenous gene is translated into protein, even with the inducible gene silencer in an active (i.e., knockout orientation), the IRES and GFP messages will not be translated as a hybrid message. FIG. 8 shows the most preferred translational stop to be used, and is abbreviated by the term TGA. This all-frame translational stop is described in the methods section of Example 1. The most preferred IRES site is also mentioned in FIG. 8, namely, a 5'UTR of the GTX homeodomain protein. Chappell, et al., describe this IRES as being superior in its activity compared to other known IRES sites, such as ECMV (see Chappell, et al., "A 9-nt segment of a cellular mRNA can function as an internal ribosome entry site (IRES) and when present in linked multiple copies greatly enhances IRES activity", PNAS, Feb. 15, 2000, volume 97, no. 4, pages 1536-1541). As suggested above, the IRES site is important so that the translation of GFP is proper, particularly if preceded by an endogenous translation start site. Finally, the most preferred polyadenylation sequence to use in our inducible gene silencer depicted in FIG. 8 is a 4X SV40 poly A. This polyadenylation sequence is discussed, for example, in Maxwell, I. H., et al., "A DNA cassette containing a trimerized SV40 polyadenylation signal which efficiently blocks spurious plasmid-initiated transcription", BioTechniques, 1989, vol. 7(3), pp. 276-280.

The GFP coding sequence provided in the inducible gene silencer set forth in FIG. 8 has a number of functions. (Most preferably, enhanced GFP or EGFP is used.) First, it provides a coding sequence of sufficient length as to mimic, in length, the terminal exon of most eukaryotic genes. We believe this is important to ensure proper processing of the transcript such that the GFP coding sequence becomes the terminal exon of the mature, processed fusion transcript. This ensures the gene silencing effect of the IGS. Secondly, the GFP sequence provides a reporter of gene expression from the IGS in the knockout orientation.

In addition, the GFP DNA sequence functions, as noted earlier, as a reporter when it is expressed as a protein. That is, when one shines fluorescent light or UV light onto this protein, it emits a green wavelength which is detectable. Consequently, we can identify those cells expressing GFP from the inducible gene silencer provided in FIG. 8. As suggested earlier, in the context of our discussion of FIG. 3, this inducible gene silencer will function only when it is in the forward orientation, as found in FIG. 8. That is, when this inducible gene silencer is provided in the reverse direction, it is in an inert orientation, and will not function in the manner described earlier in this paragraph. As already described, it is the use of mutant Lox sites provided in opposing orientation, and having different termination mutations, that allows the inducible gene silencer provided in an inert orientation in a gene to be inverted using Cre recombinase, to create the functional inducible gene silencer which allows one to conduct a conditional knockout according to our invention, for use in gene trapping or gene targeting. For example, one can insert such an inducible gene silencer into a gene of interest, allow the host organism containing the gene of interest to survive, and when one wishes to knock out the gene's function, one can use Cre recombinase to invert the inducible gene silencer, which will remain inverted and stay in the active orientation during the rest of the duration of the host cell's life.

Although in gene trapping our inducible gene silencer would be introduced randomly into a host organism, using a virally-mediated approach, in gene targeting our inducible gene silencer could be introduced into a specific gene of interest by homologous recombination. Information regarding homologous recombination in ES cells can be found in Doetschman, T., et al., "Targetted correction of a mutant HPRT gene in mouse embryonic stem cells", Nature, Dec. 10-16, 1987, vol. 330(6148), pp. 576-8, the content of which is herein incorporated by reference. See also Thomas, Kirk R., et al., "Site-directed mutagenesis by gene targeting in mouse embryo-derived stem cells", Cell, Nov. 6, 1987, vol. 51, pp. 503-512, the content of which also is herein incorporated by reference.

The DNA sequence and elements of a most preferred inducible gene silencer is depicted in FIGS. 12A to 12D. The DNA sequence for this inducible gene silencer is also set forth as SEQ ID NO: 1 in the attached sequence listing. Individual elements included in this inducible gene silencer also are set forth in the sequence listing as follows: Lox71 (SEQ ID NO: 2), splice acceptor (SEQ ID NO: 3), all-frame translational stop (SEQ ID NO: 4), GTX-IRES (SEQ ID NO: 5), EGFP (SEQ ID NO: 6), 4X- Polyadenylation sequence or 4X-PolyA) (SEQ ID NO: 7), and Lox66 (SEQ ID NO: 8). It should be noted that both the Lox66 sequences in FIG. 5 (i.e., SEQ ID NO: 14) and in FIG. 12D (i.e., SEQ ID NO: 8) are correct. The latter sequence is in the reverse orientation to the former.

In terms of the various sequences used to construct the inducible gene silencer of FIGS. 12A to 12D, the GTX-IRES site, and the EGFP and RFP sequences are available commercially from Invitrogen. Furthermore, the 4X SV40 polyadenylation sequence can be constructed as described in Maxwell, I. H., et al., "A DNA cassette containing a trimerized SV40 polyadenylation signal which efficiently blocks spurious plasmid-initiated transcription", BioTechniques, 1989, vol. 7(3), pp. 276-280, the content of which is herein incorporated by reference. Also, the Lox sites, the TGA site, and the Frt sites were prepared using PCR, in accordance with conventional methods known to those skilled in the art. (Additional information regarding these methods are also provided in our discussion of Examples below.) Finally, Cre recombinase and Flp recombinase genes are available from Invitrogen and Gene Bridges, respectively.

While we envision that our inducible gene silencer will function so long as it contains a pair of recombination sites that have an activity similar to the ones depicted in FIG. 8, a splice acceptor, an IRES site, a reporter gene, and a polyadenylation sequence, the actual identity of each of these elements is variable and could include any such elements known by those skilled in the art. The translational stop sequence, if used at all, can be any sequence that will stop translation in all three reading frames. (The translational stop, as suggested earlier, is an element that can be deleted from the inducible gene silencer of FIG. 8, while still retaining the desired activity of the inducible gene silencer.) For example, the IGS constructed as described in Example 1 (and shown schematically in FIG. 8) contains a 6X-translational stop sequence which is a synthetic sequence we designed, comprised of six stop codons in tandem separated by single nucleotides between each codon so as to place two stop codons in each translational reading frame.

Figure 1:
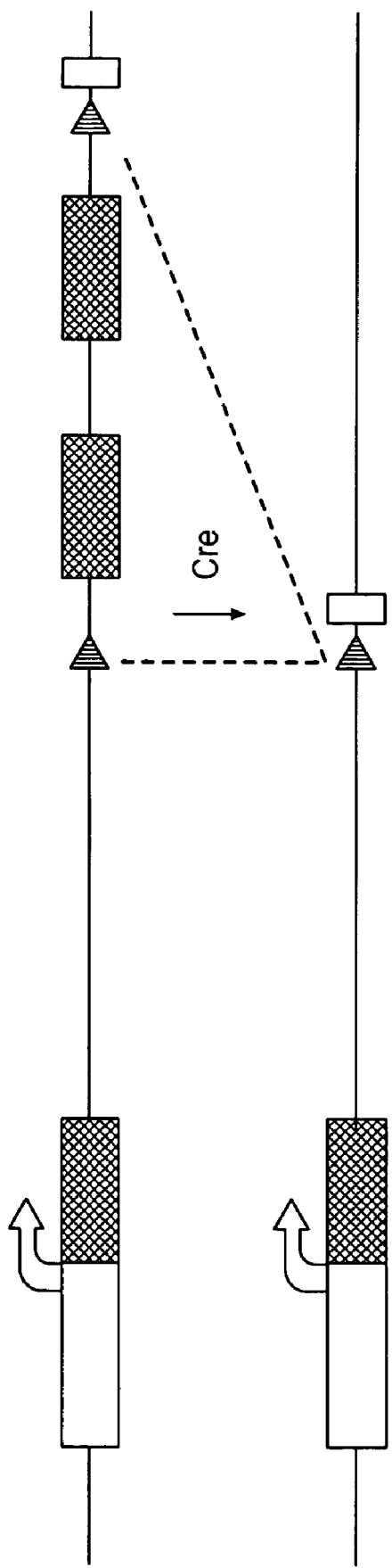
FIG. 1 shows two alleles subjected to a conventional deletion-based conditional knockout strategy.

As noted earlier, we believe our inducible gene silencer to be unique over previously known genetic constructs. For example, we find that the constructs provided in U.S. Pat. No. 6,136,566 to Sands, et al. differ from our inducible gene silencer, for example, in that no recombination sites are provided at the edges of the Sands, et al. construct. As noted on numerous occasions, it is the existence of such recombination sites, such as the Lox sites having termination mutations, that is critical to the proper functioning of our inducible gene silencer, including its ability to lie dormant in a gene, when in the inert orientation, and become active in the knockout orientation, upon recombinase-mediated inversion. Moreover, we find our inducible gene silencer to be different from the exchangeable gene trap using mutated Lox sites that is described in the article by Araki, et al., entitled "Exchangeable gene trap using the Cre/mutated Lox system", Cellular and Molecular Biology, 1999, volume 45(5), pages 737-750. That reference describes a vector by which random insertional mutagenesis can be conducted as the first step, and then a β-geo gene can be replaced with any gene of interest using Cre-mediated integration. As shown in FIG. 1 of that reference, the genetic construct used by Araki, et al., involves the use of both wild-type and mutant Lox sites provided in the same direction so as to cause deletion of a gene, or integration of a new gene. Finally, our inducible gene silencer is different from that described in the Zhang, et al., reference noted earlier which speaks of using of Cre recombinase-mediated inversion to introduce conditional point mutations into the CREB-binding protein.

Figure 13:
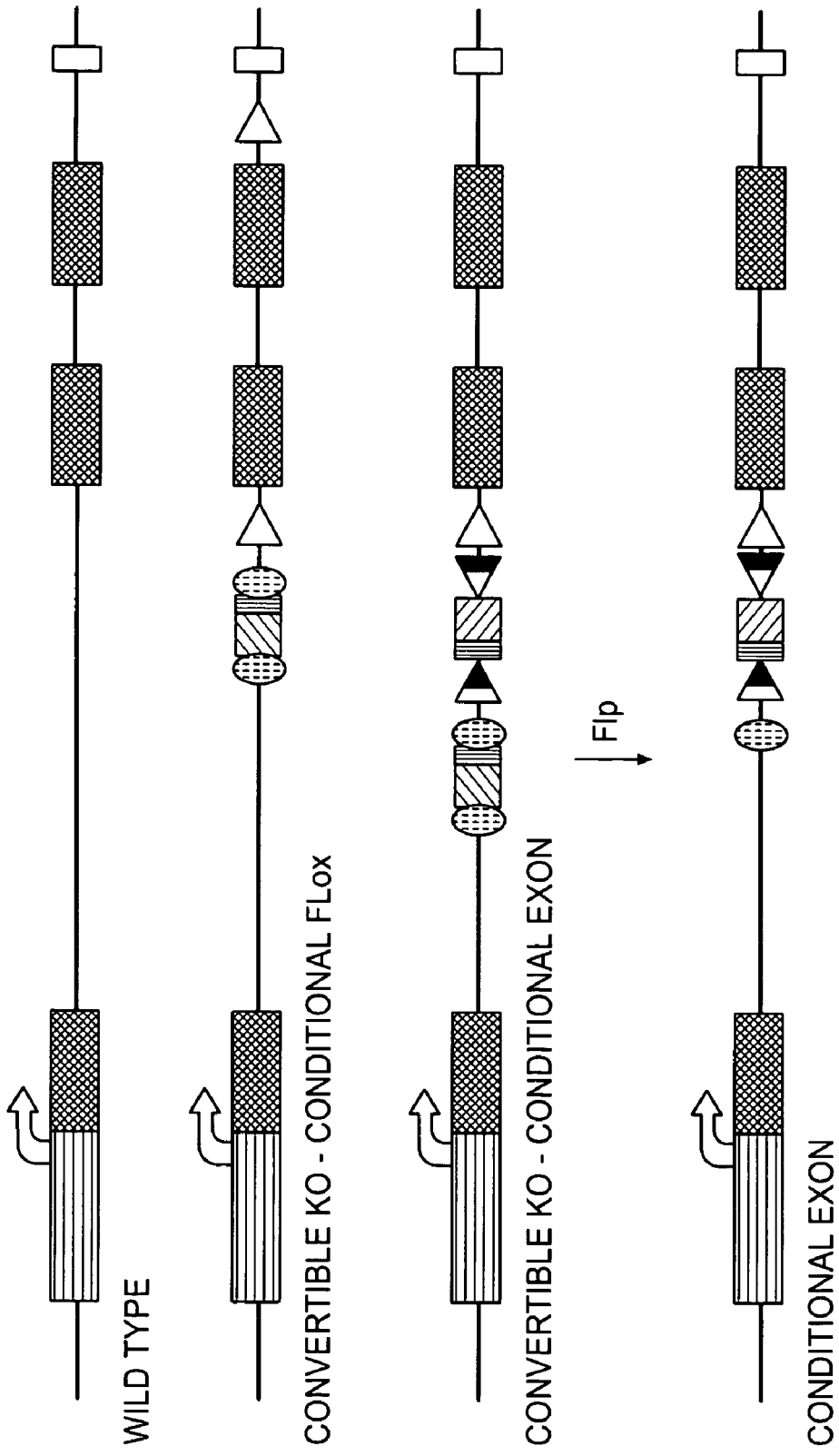
FIG. 13 shows alleles subjected to a convertible knockout gene trapping and gene targeting strategy.

An alternative embodiment of our invention is depicted in FIG. 13. The figure illustrates different gene targeting schemes that we term "convertible knockouts". Each scheme uses a different approach to engineer elements into a gene of interest that first knock out the gene, and then can be converted, by site-specific recombinase, to conditional knockouts. The first allele shown in FIG. 13 is a wild-type allele, with no genetic constructs inserted therein. The second allele, however, contains a combination of knockout elements creating the convertible knockout. For example, a gene silencing element flanked by two Frt sites can be included in the intron space between the first and second exons of this gene. Upon the addition of Flp recombinase, this element can be deleted. Also in this second allele, one can include a pair of wild type Lox sites provided in the same orientation, so as to effect a deletion-based conditional knockout of the gene by deletion of the second and third exons, as described earlier in this application.

Most interestingly, as shown in the third allele, one can combine a gene silencing element flanked by Frt sites, which will function as described with regards to the second allele upon the addition of Flp recombinase. This third allele can also include an inducible gene silencer, such as described in FIG. 8, which, upon the addition of Cre recombinase, can be inverted to render the sequence therein active. Finally, one might also include, in the third allele, a Lox site containing a core or compatibility mutation, such that the gene sequence within which it is inserted can undergo a recombinase mediated cassette exchange with a second genetic sequence located proximally to the first, and preferably containing a second mutated Lox site, which also has a core or compatibility mutation. Additional information regarding a preferred recombinase mediated cassette exchange is provided in our discussion which follows with regards to FIGS. 14A and 14B. We envision that the various elements described with regards to FIG. 13 can be assembled in various combinations to achieve the desired result.

Figure 14A:
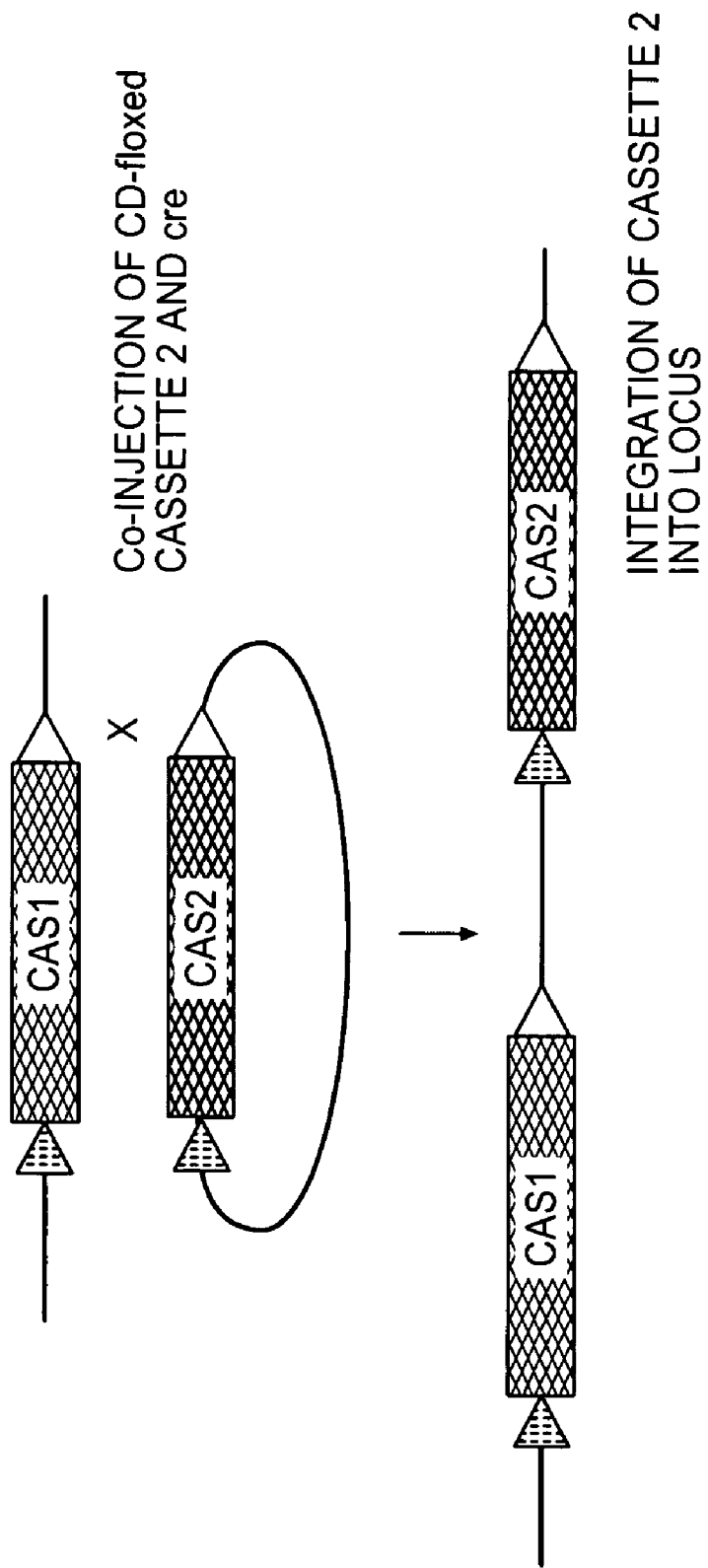
FIG. 14A shows a schematic of the first step in a Cre recombinase mediated cassette exchange.
Figure 14B:
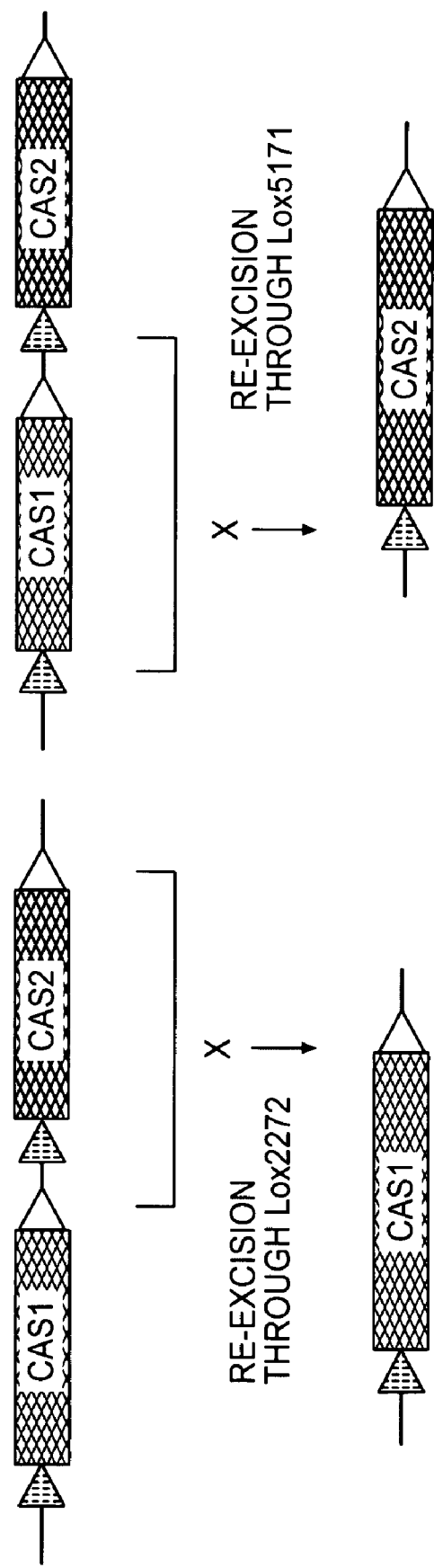
FIG. 14B shows a schematic of the second step in a Cre recombinase mediated cassette exchange.

FIGS. 14A and 14B shows a schematic of the two step process by which a preferred recombinase mediated cassette exchange can occur. Most preferably, optimal operation of this exchange event occurs with the use of two sets of mutant Lox sites each containing different mutations in the core or palindromic sequence. When different core mutations exist in each Lox site in a pair, these sites cannot recombine. Instead, what occurs is a replacement of one DNA sequence for another by a two-step process, as shown in FIGS. 14A and 14B. More specifically, FIG. 14A shows cassette 1 flanked by two Lox sites in the same orientation, but each containing a different core mutation (i.e., Lox5171 and Lox2272). Proximally located to this linear piece of DNA is a circular piece of DNA containing a cassette 2 sequence, also flanked by two Lox sites in the same orientation, each having a different core mutation (i.e., also Lox5171 and Lox2272). Upon injecting Cre recombinase into the system, cassette 2 is integrated into the locus at which cassette 1 is located. Next, in FIG. 14B, the darkly shaded triangles, which are Lox2272 sites, cause cassette 2 to be deleted. Moreover, the pair of Lox5171 sites cause deletion of cassette 1. In this manner, the DNA sequences can be exchanged.

Finally, FIG. 15 provides a schematic of a method by which site-directed transgenics could be used to test whether the recombinase mediated cassette exchange described generally in FIGS. 14A and 14B has occurred properly. As described in FIG. 15, first one needs to develop a GFP transgene with flanking Lox sites, a β-actin promoter and a CMV enhancer. This sequence can be referred as a "landing pad". Second, this landing pad construct can be microinjected into a mouse. Third, this mouse containing the landing pad construct can be crossbred with a wild-type mouse. The resulting progeny can be screened for desired gene expression from the landing pad construct. Thereafter, embryos can be collected from the selected landing pad transgenic animals before cleavage. Next, a combination of Cre recombinase and transgene (i.e., red fluorescent protein or RFP) can be co-injected into the embryos before nuclear fusion. Finally, genotyping of the GFP landing pad and replacement transgenes (i.e., RFP) can be conducted to identify site directed transgenic animals, as shown in the bottom four mice illustrated in FIG. 15.

The following Examples are merely illustrative of the present invention and are not to be considered as limiting the invention, which is properly delineated in the following claims.

EXAMPLE 1

Construction of the Inducible Gene Silencer (IGS) Element and In Vitro Testing of this Element for CRE-Mediated Inversion In this example, we prepared the inducible gene silencer (IGS) element, shown in FIGS. 12A to 12D, using standard recombinant techniques. Also, in this example, we verified whether the inducible gene silencer shown in FIGS. 12A to 12D inverted correctly upon the addition of Cre recombinase in vitro. The following materials and methods were used in these experiments.

Construction of an Inducible Gene Silencer (IGS). An inducible gene silencer (IGS) was constructed in the pBluescript II SK+ plasmid (pBS-SK+), available from Stratagene. Lox66 and Lox71 sites were placed into pBS-SK+ by annealing single stranded oligonucleotides and ligating them into the XhoI and Hind III sites, respectively, to generate pBS-lox66,71. The oligonucleotide sequences 5'TCGAGTAC-CGTTCGTATAGCATACATTATACGAAGTTATC (SEQ ID NO: 15) and 5'TCGAGATAACTTCGTATAATGTATGC-TATACGAACGGTAC (SEQ ID NO: 16) were used to prepare Lox71, and the oligonucleotide sequences 5'AGCTT-TACCGTTCGTATAATGTATGCTATACGAAGTTATA (SEQ ID NO: 17) and 5'AGCTTATAACTTCGTATAG-CATACATTATACGAACGGTAA (SEQ ID NO: 18) were used to prepare Lox66. The splice acceptor of the adenovirus major late transcript was released from pSAbeta-geo (a gift from Philip Soriano) as a BamHI/PstI fragment and ligated into the BamHI/PstI site of pBS-SK+. (Plasmid pSAbeta-geo is described in Friedrich, G. & Soriano, P., "Promoter traps in embryonic stem cells: a genetics screen to identify and mutate developmental genes in mice," Genes & Development, 1991, vol. 5(9), pp. 1513-1523. Also, BamHI/PstI restriction endonucleases are available from New England Biolabs.) The Gtx-IRES was amplified by PCR to contain flanking PstI sites and six copies of translation stop codons intervening the 5' PstI site and the 5' end of the IRES and cloned into the pGEM-T Easy vector, available from Promega. Primer sequences 5'CTGCAGGTCTGACTAAC-TAGCTAGCTAAGTGAATATGGTCGACCTGC AGGCG (SEQ ID NO: 19) and 5'CTGCAGTGCTCCCGGCCGC-CATGG (SEQ ID NO: 20) were used. The entire 6X-stop-IRES fragment was ligated into the PstI site, 3' of the splice acceptor. The 6X-stop sequence (TGACTAAC-TAGCTAGCTAAGTGAA) within the primer (SEQ ID NO: 19) shown above, is a synthetic sequence we designed and is comprised of six stop codons in tandem separated by single nucleotides between each codon so as to place two stop codons in each translational reading frame (see FIG. 12A). EGFP was removed from PCX-EGFP as an EcoRI fragment and ligated 3' of the IRES into the EcoRI site. (Plasmid pCX-EGFP is described in Niwa, et al., "Efficient selection for high-expression transfectants with a novel eukaryotic vector", Gene, 1991, vol. 108, pp. 193-200, the content of which is herein incorporated by reference.) A DNA cassette containing four copies of the SV40 polyadenylation sequence was removed from pUC.A.1.5 as a Hind III fragment and ligated 3' of the EGFP. (Plasmid pUC.A.1.5 is described in Maxwell, I. H., et al., "A DNA cassette containing a trimerized SV40 polyadenylation signal which efficiently blocks spurious plasmid-initiated transcription", BioTechniques, 1989, vol. 7(3), pp. 276-280, the content of which is herein incorporated by reference. Also, HindIII restriction endonuclease is available from New England Biolabs.) The entire splice acceptor/ 6X-stop/IRES/EGFP/4X-polyA was removed as a BamHI fragment and ligated into the BamHI site of pBS-lox66,71 to create pBS-IGS. The final structure of the IGS is provided in FIGS. 12A to 12D.

In vitro testing of this element for Cre-mediated inversion. The following methods were used to test Cre-mediated inversion of the inducible gene silencer by reacting pBS-IGS with Cre recombinase in vitro. An in vitro reaction was performed to test the ability of the IGS to invert in the presence of Cre-recombinase according to the manufacturer's (Clonetech) protocol. In vitro inversion was scored using an NcoI restriction fragment pattern analysis that distinguishes between the inverted and non-inverted IGS clones following exposure to Cre activity in vitro. DNA that had undergone the Cre-reaction was transformed into E. coli and DNA was subsequently isolated from individual colonies and screened by NcoI digestion.

Figure 9B:
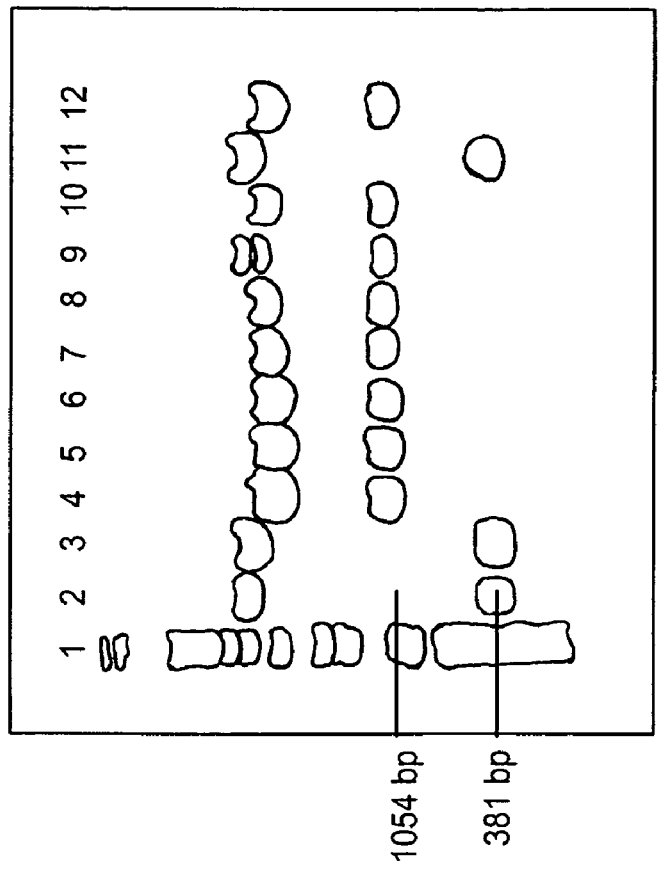
FIG. 9B shows a restriction pattern analysis of the inducible gene silencer of FIGS. 12A to 12D in various test samples, digested by NcoI.
Figure 9A:
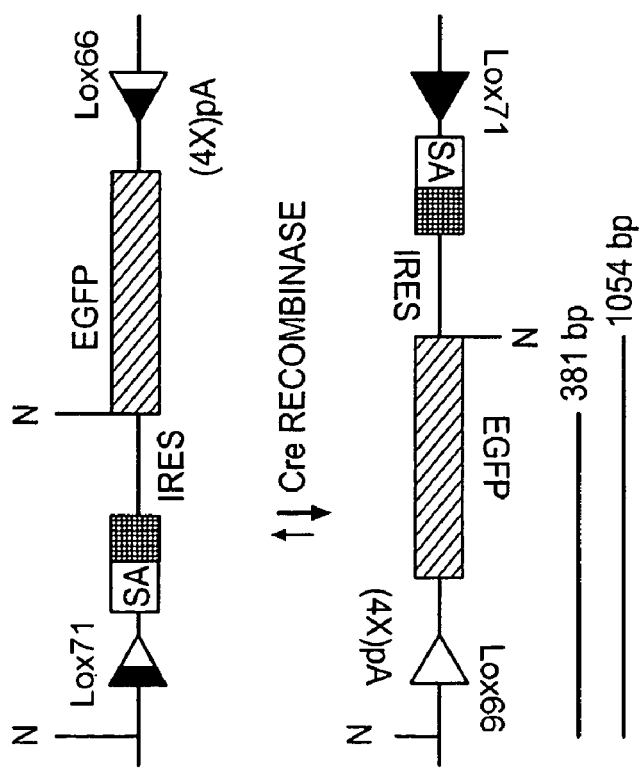
FIG. 9A shows a schematic of the inducible gene silencer of FIGS. 12A to 12D in an inert and then a knockout orientation, as well as the NcoI restriction sites, and fragments resulting from an NcoI digestion.

FIG. 9A shows a schematic of the inducible gene silencer of FIGS. 12A to 12D in an inert orientation and then in a knockout orientation, as well as the NcoI restriction sites, and fragments resulting from NcoI digestion. FIG. 9B shows an NcoI restriction pattern analysis of the inducible gene silencer of FIGS. 12A to 12D from 11 samples, digested with NcoI. Plasmid pBS-IGS in the inert orientation releases 4015 bp and 381 bp bands, whereas the inverted pBS-IGS produces bands of 3342 bp and 1054 bp. As can be seen in FIG. 9B, the mutant Lox sites in the inducible gene silencer of FIGS. 12A to 12D led to Cre-mediated inversion in 7 of the 11 samples. Samples 4, 5, 6, 7, 8, 10 and 12 exhibit the 1054 bp NcoI band, diagnostic of the inverted pBS-IGS, indicating that Cre mediated recombination induces inversion of the inducible gene silencer.

EXAMPLE 2

Functional Testing of the Inducible Gene Silencer by Transient Expression in Mouse Embryonic Fibroblasts After constructing the inducible gene silencer of FIGS. 12A to 12D, we conducted some functional tests with the inducible gene silencer inserted into various reporter plasmids. The materials and methods that we used for this experiment, as well as the results are provided below.

Testing the silencing activity of the inducible gene silencer with a reporter plasmid transiently transfected into mouse fibroblasts. The IGS was subcloned in both the inert and knockout orientations into the XbaI site of the intron of the reporter construct PCX-RFP as an NheI fragment to generate pCX-IGS$^{Inert}$-RFP and pCX-IGS$^{KO}$-RFP. The reporter plasmids were transfected into primary mouse embryonic fibroblast (MEF) cells using lipofectamine reagent (Invitrogen). Control plasmids pCX-EGFP and pCX-RFP were used to control for expression and detection of the RFP and GFP fluorescent reporters. Fluorescence microscopy was used to visualize the expression of GFP and RFP in transiently transfected cells.

Figure 10:
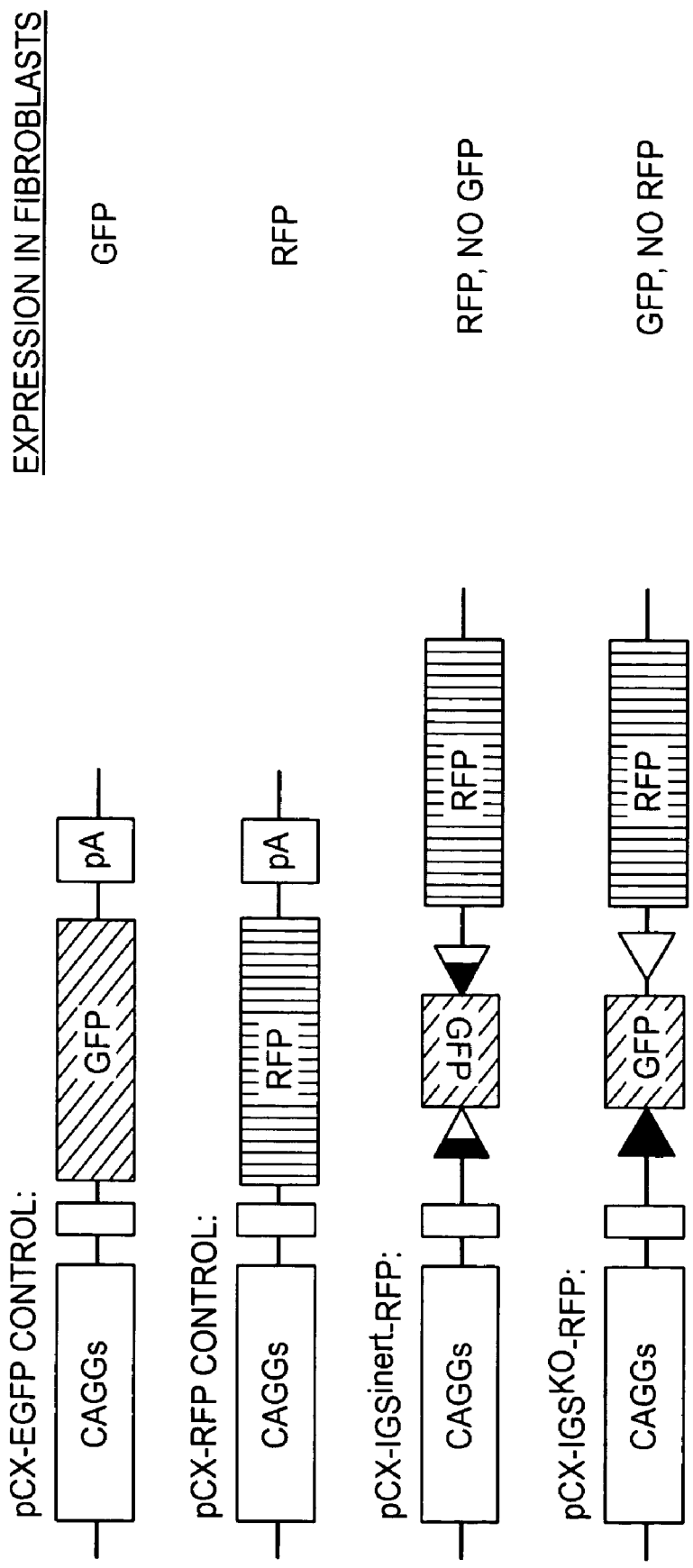
FIG. 10 shows the genetic constructs used in the functional testing of the inducible gene silencer of FIGS. 12A to 12D, as well as the results of such functional testing.

FIG. 10 illustrates the control and test constructs used in the transient transfection assay as well as indicating the expected results. While the two test constructs of FIG. 10 (i.e., pCX-IGS$^{inert}$-RFP and pCX-IGS$^{KO}$-RFP) shown schematically in FIG. 10 are only labelled as containing "GFP" between the Lox sites, it is to be understood that each construct contains all necessary elements required to make a properly functioning inducible gene silencer, as described previously. FIGS. 11A to 11F show fluorescent gene expression results for control and test constructs transiently transfected into mouse embryonic fibroblasts. FIGS. 11A and 11B show GFP and RFP expression from the pCX-EGFP and pCX-RFP control constructs, respectively, indicating expression and detection from these reporter constructs. FIGS. 11C and 11D show that the PCX-IGS$^{inert}$-RFP construct expresses RFP but not GFP in transiently transfected mouse embryonic fibroblasts, indicating that, in the inert orientation, the inducible gene silencer does not silence the host gene (RFP) and does not express the IGS reporter gene (GFP). However, FIGS. 11E and 11F show that the pCX-IGS$^{KO}$-RFP construct expresses GFP but not RFP in transiently transfected mouse embryonic fibroblasts, indicating that, in the knockout orientation, the inducible gene silencer silences the host gene (RFP) and simultaneously expresses the IGS reporter gene (GFP).

EXAMPLE 3

Functional Testing of the Conditional Exon by Gene Targeting of the HPRT Locus in ES Cells In order to test the inducible gene silencer for its ability to inducibly silence a target gene, we targeted this element to the HPRT locus in mouse ES cells and evaluated the function of this element in both the inert and the KO orientation. The methods used in these studies are as follows.

Methods: Construction of the HPRT-IGS Targeting Vector. An HPRT targeting vector was generated by inserting the IGS as a BamHI fragment, in the inert orientation, by blunt end ligation into the EcoRV restriction site in intron one of the HPRT genomic clone, pBS-HPRT6.5 (a gift from Peter Detloff). (Plasmid pBS-HPRT6.5 is described in Ordway, Jared M., et al., "Ectopically expressed CAG repeats cause intranuclear inclusions and a progressive late onset neurological phenotype in the mouse", Cell, Dec. 12, 1997, vol. 91, pp. 753-763, the content of which is herein incorporated by reference.) A Frt flanked neomycin resistance gene was also placed adjacent to the IGS to allow G418 selection into mouse embryonic stem cells after electroporation of the targeting construct. (Information regarding the use of the Frt/Flp system in gene targeting can be found in Meyers, E. N., et al., "An Fgf8 mutant allelic series generated by Cre- and Flp-mediated recombination", Nature Genetics, February 1998, vol. 18(2), pp. 136-41, the content of which is herein incorporated by reference.)

Southern blot analysis screening for HPRT-IGS gene targeted ES cells. A 230 bp HPRT Southern probe, external to the targeting vector sequence and spanning exon/intron three, was generated by PCR amplification of mouse genomic DNA using the following primers:

5'TTTCTATAGGACTGAAAGAC      (SEQ ID NO: 21)    and

5'CCTATTTTTTAATTATAAG.      (SEQ ID NO: 22)

DNA was prepared from G418-resistant ES cell colonies and screened for targeted integration by digestion with SacI restriction endonuclease (New England Biolabs), Southern blotting, and hybridization with the HPRT probe.

HAT Selection of Targeted ES Cells. Targeted clone G10 was subsequently placed under HAT (hypoxanthine, aminopterin, thymidine)-selection. HAT-selection kills cells not expressing HPRT. Clone G10 survived under HAT-selection, indicating that the inert-placed IGS did not knock out endogenous HPRT expression.

Figure 17B:
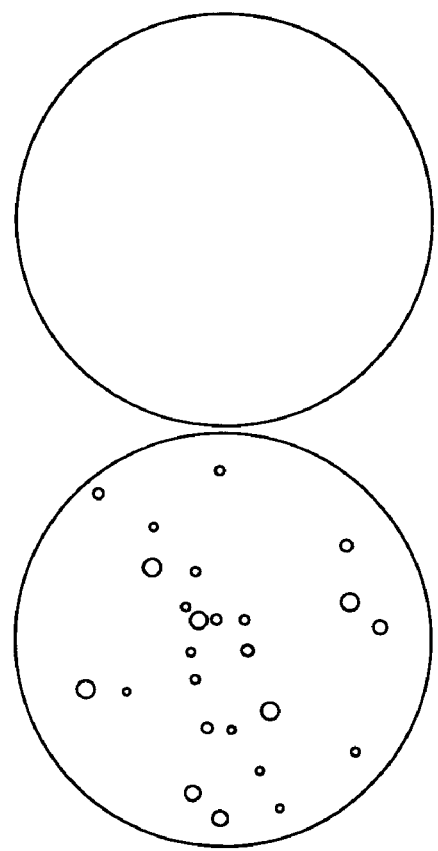
FIG. 17B shows targeted clone G 10 cells transfected with the pCAGGS-Cre plasmid (left plate) or mock transfected with an empty pCAGGS plasmid(right plate).
Figure 18:
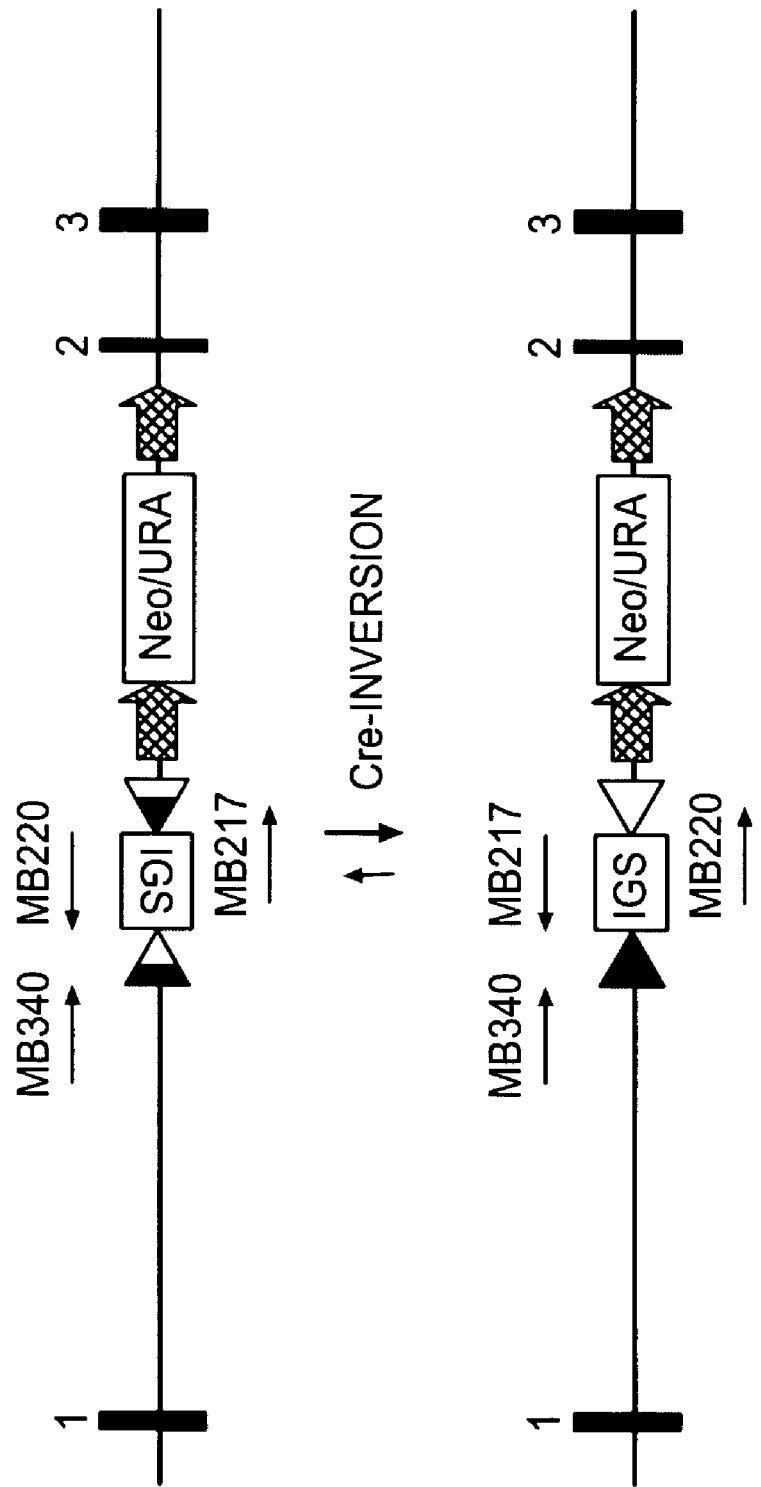
FIG. 18 shows a schematic of the location of primer sequences MB 340, MB 220 and MB 217 in relation to the inducible gene silencer in the inert and active orientations.

Inversion of the IGS in Targeted ES Cells. Targeted clone G10 was electroporated with the plasmid pBS 185 (i.e., pCAGGS-Cre) or mock transfected with empty pCAGGS plasmid. Cells were plated in serial dilutions and placed under 6-Thioguanine (6-TG)- or no selection. 6-TG kills cells that express HPRT. Cells transfected with pBS185 (i.e., pCAGGS-Cre) generated numerous 6-TG-resistant colonies, while the ES cells transfected with empty plasmid generated none, as shown in FIG. 17B. This suggests that the 6-TG resistant cells were the result of Cre-mediated inversion of the IGS, and silencing the result of HPRT rather than 6TG resistance due to spontaneous mutations in the HPRT gene. A Cre- and mock-transfected plate under 6-TG-selection were stained with a 0.33% methylene blue/methanol solution to visualize colony formation on the plates. A total of 96 colonies were picked, 48 6-TG selected and 48 non selected and screened by PCR. By conducting an analysis using gel electrophoresis, we found that primers MB340 (5'CTATACA-GAGAAATCCTGCC) (SEQ ID NO: 23) and MB220 (5'CACTCTCGGCATGGACGAGC) (SEQ ID NO: 24) primed PCR amplification only if the IGS did not invert, whereas primers MB340 and MB217 (5'CGGACACGCT-GAACTTGTGG) (SEQ ID NO: 25) primed PCR amplification only if the Cre-mediated IGS inversion occurred. Locations of these primer sequences in relation to the IGS are shown in FIG. 18.

Figure 16:
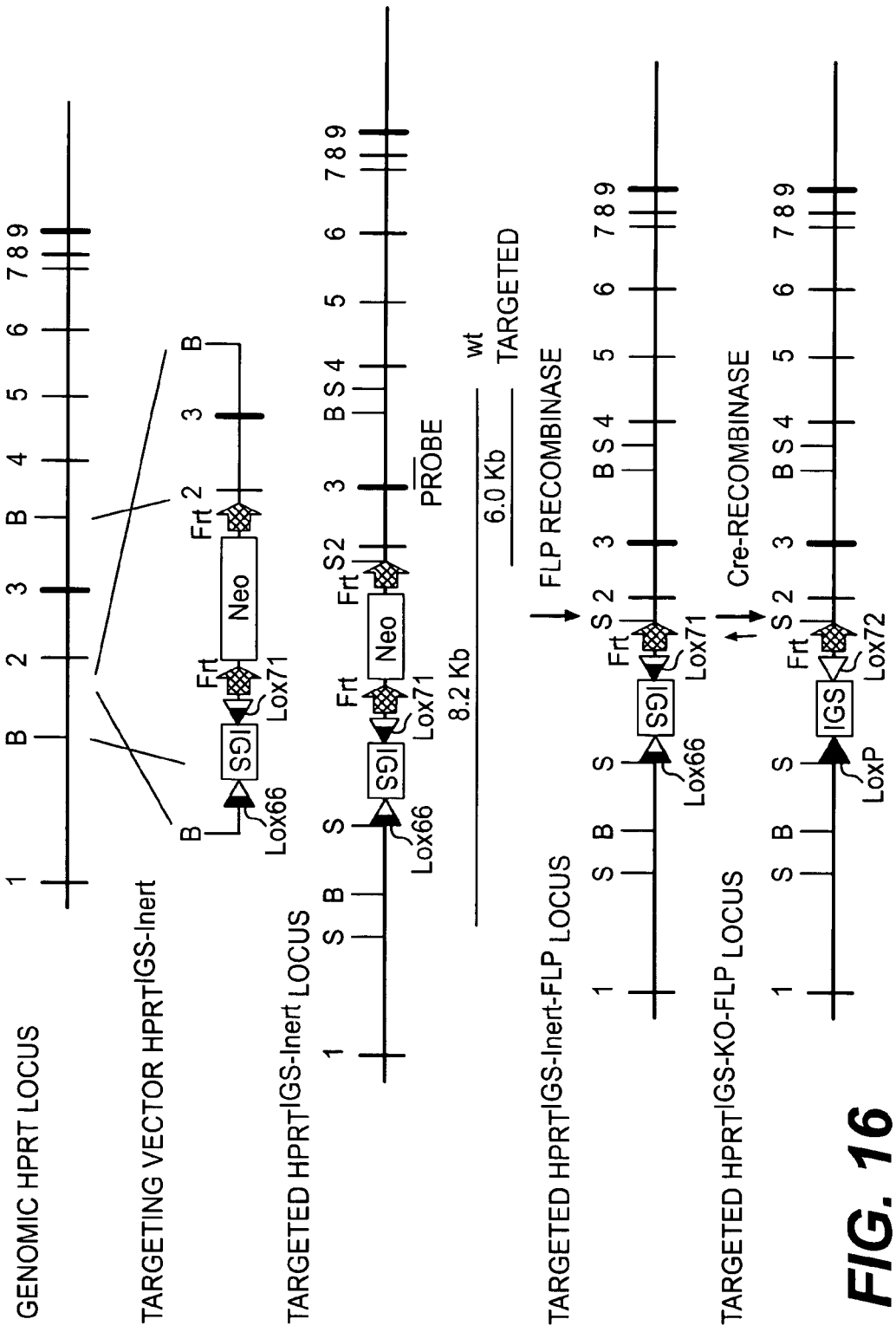
FIG. 16 shows a schematic of an HPRT-IGS targeting vector, and the results of adding Flp and Cre recombinase to this vector.
Figure 17A:
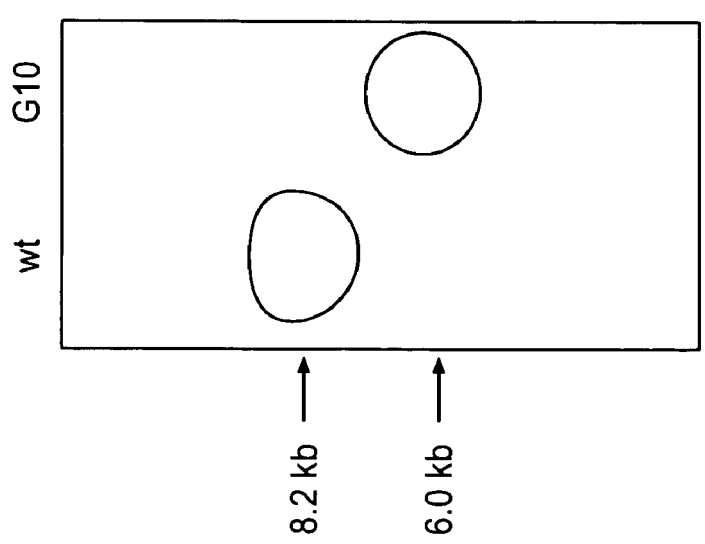
FIG. 17A shows a Southern blot analysis screening for HPRT-IGS targeted ES cells.

Results: FIG. 16 illustrates the targeting of the inducible gene silencer to intron one of the HPRT locus in ES cells. More specifically, this figure indicates the structure of the wild type HPRT locus, the structure of the gene targeting vector with the IGS in the inert orientation, and the final structure of the HPRT locus containing the IGS in the inert orientation. The probe used to identify properly targeted ES cells is also indicated, as well as the diagnostic 8.2 kb and 6.0 kb genomic SacI fragments of the wt and targeted HPRT loci, respectively. FIG. 17A shows the results of a Southern blot analysis, indicating a wild type 8.2 kb band from a non-targeted ES cell clone and the 6.0 kb band of a gene targeted ES cell clone number G110.

The gene targeted G10 ES cell clone was expanded and tested for the effect of the IGS in the inert orientation on expression of the HPRT host gene (data not shown). Both wild type and G10 cells selected in HAT medium, which kills cells not expressing HPRT, survived selection indicating that the IGS in the inert orientation does not knock out HPRT function.

Next, we tested the ability of the IGS to invert and silence the targeted HPRT gene. As described in the methods, G10 cells were expanded, transfected with the Cre expressing plasmid pBS 185 (Invitrogen), and selected in 6-Thioguanine (6TG) which kills cells that express HPRT. FIG. 17B shows a methylene blue stained culture plate showing that the Cre-transfected plate had cells that survived 6TG selection but that the mock-infected plate had no surviving cells, indicating that Cre-mediated inversion had knocked out HPRT expression in the Cre-transfected cells.

Finally, to prove to ourselves that the IGS had truly inverted in the 6TG resistant ES cells, we performed PCR amplification using primers (as shown in FIG. 18) that distinguish between the inert and KO orientations of IGS in the targeted HPRT locus. Our experimental results, not shown, indicated that the IGS did indeed invert in the ES cells resistant to 6TG selection.

These results together confirm that the IGS targeted to an endogenous gene in the inert orientation does not knock out expression of the host gene and that the IGS can be induced, by Cre-mediated recombination, to invert and knock out expression of the host gene.

This invention is useful not only as a research tool, but also may be useful in creating better controls for gene therapy.

While particular embodiments of the present invention have been illustrated and described, it will be apparent to those skilled in the art that various changes and modifications may be made without departing from the spirit and scope of the invention. Furthermore, it is intended that the claims will cover all such modifications that are within the scope of the invention.

We claim:

1. An inducible gene silencer set forth in SEQ ID NO:1.
2. A vector comprising the inducible gene silencer set forth in claim 1 in an active orientation.
3. A vector comprising the inducible gene silencer set forth in claim 1 in an inert orientation.
4. An isolated embryonic stem (ES) cell comprising the vector of claim 2.
5. An isolated embryonic stem (ES) cell comprising the vector of claim 3.
6. A conditional knockout gene trapping or gene targeting method comprising the steps of:
    (a) inserting the inducible gene silencer of claim 1 into a vector in an inert orientation;
    (b) transfecting the vector comprising the inducible gene silencer into a host cell;
    (c) delivering a suitable recombinase enzyme, or a polynucleotide encoding a suitable recombinase enzyme, to the transfected host cell in vitro, at any desired time, to cause the inducible gene silencer to invert into an active orientation, such that the inducible gene silencer knocks out the functioning of a gene into which it has inserted, and expresses a reporter protein.
7. The method of claim 6, wherein the suitable recombinase enzyme in step (c) is Cre recombinase.
8. The method of claim 6, wherein the host cell is an ES cell.
9. A method of knocking out the expression of a gene of interest at a future point in time, comprising the steps of:
    (a) inserting the inducible gene silencer of claim 1 into an intron of the gene of interest in an inert orientation; and
    (b) exposing the gene of interest containing the inducible gene silencer to a recombinase enzyme in vitro at the future point in time, such that the inducible gene silencer inverts to an active orientation, thereby causing the gene of interest to cease normal expression.
10. The method of claim 9, wherein the recombinase enzyme in step (b) is Cre recombinase.
11. A eukaryotic gene comprising, within its introns, a first inducible gene silencer, according to SEQ ID NO: 1 set forth in claim 1, in combination with one or more exogenous elements selected from the group consisting of:
    (a) a second inducible gene silencer comprising either a splice acceptor and a selection marker or a splice acceptor and a reporter protein, flanked by Frt sites;
    (b) a Lox site containing a core mutation; and
    (c) a pair of Lox sites, each placed in the same orientation within different introns, such that the pair of Lox sites flanks one or more exons.
12. An inducible gene silencer comprising the sequence set forth from nucleotides 120 to 2050 of SEQ ID NO:1.
13. A conditional knockout gene trapping or gene targeting method comprising the steps of:
    (a) inserting the inducible gene silencer of claim 1 into a vector in an inert orientation;
    (b) transfecting the vector comprising the inducible gene silencer into a host cell, wherein the host cell is a mouse ES cell;
    (c) delivering a suitable recombinase enzyme, or a polynucleotide encoding a suitable recombinase enzyme, to a mouse developed from the host cell, at any desired time, to cause the inducible gene silencer to invert into an active orientation, such that the inducible gene silencer knocks out the ftinctioning of a gene into which it has inserted, and expresses a reporter protein.
14. The method of claim 13, wherein the suitable recombinase enzyme in step (c) is Cre recombinase.
15. A method of knocking out the expression of a gene of interest at a future point in time, comprising the steps of:
    (a) inserting the inducible gene silencer of claim 1 into an intron of the gene of interest in an inert orientation;
    (b) transfecting a vector containing the gene of interest comprising the inducible gene silencer into a mouse ES cell; and
    (c) exposing the gene of interest in a mouse developed from the ES cell to a recombinase enzyme at the future point in time, such that the inducible gene silencer inverts to an active orientation, thereby causing the gene of interest to cease normal expression.
16. The method of claim 15, wherein the recombinase enzyme in step (c) is Cre recombinase.

* * * * *

UNITED STATES PATENT AND TRADEMARK OFFICE
CERTIFICATE OF CORRECTION

PATENT NO. : 7,625,755 B2 Page 1 of 1
APPLICATION NO. : 10/448395
DATED : December 1, 2009
INVENTOR(S) : Askew et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 351 days.

Signed and Sealed this

Second Day of November, 2010

David J. Kappos
*Director of the United States Patent and Trademark Office*

SEQUENCE LISTING

```
<160> NUMBER OF SEQ ID NOS: 25

<210> SEQ ID NO 1
<211> LENGTH: 2133
<212> TYPE: DNA
<213> ORGANISM: Artificial
<220> FEATURE:
<223> OTHER INFORMATION: synthetic nucleic acid

<400> SEQUENCE: 1
aaaacgacgg ccagtgaatt gtaatacgac tcactatagg gcgaattggg cccgacgtcg      60
catgctcccg gccgccatgg cggccgcggg aattcgatta aggcgccgct agcggatcca     120
taacttcgta taatgtatgc tatacgaacg gtaatctgta gggcgcagta gtccagggtt     180
tccttgatga tgtcatactt atcctgtccc ttttttttcc acagctcgcg gttgaggaca     240
aactcttcgc ggtctttcca gtggggatcg acggtatctg caggtctgac taactagcta     300
gctaagtgag caggcggccg cgaattcttc tgacatccgg cgggttttctg acatccggcg     360 ggtttctgac atccggcggg tttctgacat ccggcgggtt tctgacatcc ggcgggtgac     420
```

-continued

```
tcacaacccc agaaacagac atccatggcg gccgggagca atgcactgca gatgcagctg    480
caggaattcg ccaccatggt gagcaagggc gaggagctgt tcaccggggt ggtgcccatc    540
ctggtcgagc tggacggcga cgtaaacggc cacaagttca gcgtgtccgg cgagggcgag    600
ggcgatgcca cctacggcaa gctgaccctg aagttcatct gcaccaccgg caagctgccc    660
gtgccctggc ccaccctcgt gaccaccctg acctacggcg tgcagtgctt cagccgctac    720
cccgaccaca tgaagcagca cgacttcttc aagtccgcca tgcccgaagg ctacgtccag    780
gagcgcacca tcttcttcaa ggacgacggc aactacaaga cccgcgccga ggtgaagttc    840
gagggcgaca ccctggtgaa ccgcatcgag ctgaagggca tcgacttcaa ggaggacggc    900
aacatcctgg ggcacaagct ggagtacaac tacaacagcc acaacgtcta tatcatggcc    960
gacaagcaga agaacggcat caaggtgaac ttcaagatcc gccacaacat cgaggacggc   1020
agcgtgcagc tcgccgacca ctaccagcag aacaccccca tcggcgacgg ccccgtgctg   1080
ctgcccgaca accactacct gagcacccag tccgccctga gcaaagaccc caacgagaag   1140
cgcgatcaca tggtcctgct ggagttcgtg accgccgccg ggatcactct cggcatggac   1200
gagctgtaca agtaagaatt cgatatcaag cttgcagatc tgcgactcta gaggatctgc   1260
gactctagag gatcataatc agccatacca catttgtaga ggttttactt gctttaaaaa   1320
acctcccaca cctcccctg aacctgaaac ataaaatgaa tgcaattgtt gttgttaact   1380 tgttattgc agcttataat ggttacaaat aaagcaatag catcacaaat ttcacaaata   1440
aagcattttt ttcactgcat tctagttgtg gtttgtccaa actcatcaat gtatcttatc   1500
atgtctggat ctgcgactct agaggatcat aatcagccat accacatttg tagaggtttt   1560
acttgcttta aaaaacctcc cacacctccc cctgaacctg aaacataaaa tgaatgcaat   1620
tgttgttgtt aacttgttta ttgcagctta taatggttac aaataaagca atagcatcac   1680
aaatttcaca aataaagcat ttttttcact gcattctagt tgtggtttgt ccaaactcat   1740
caatgtatct tatcatgtct ggatctgcga ctctagagga tcataatcag ccataccaca   1800
tttgtagagg ttttacttgc tttaaaaaac ctcccacacc tccccctgaa cctgaaacat   1860
aaaatgaatg caattgttgt tgttaacttg tttattgcag cttataatgg ttacaaataa   1920
agcaatagca tcacaaattt cacaaataaa gcatttttt cactgcattc tagttgtggt   1980
ttgtccaaac tcatcaatgt atcttatcat gtctggataa cttcgtatag catacattat   2040
acgaacggta ggatccacgc gtgctagcaa ttcgatatca ctagtgaatt cgcggccgcc   2100
tgcatagctt gagtattcta tagtgtcacc taa                                2133
```

<210> SEQ ID NO 2
<211> LENGTH: 34
<212> TYPE: DNA
<213> ORGANISM: Artificial
<220> FEATURE:
<223> OTHER INFORMATION: synthetic nucleic acid

<400> SEQUENCE: 2
ataacttcgt ataatgtatg ctatacgaac ggta                                34

<210> SEQ ID NO 3
<211> LENGTH: 129
<212> TYPE: DNA
<213> ORGANISM: Simian virus 40

<400> SEQUENCE: 3

```
atctgtaggg cgcagtagtc cagggtttcc ttgatgatgt catacttatc ctgtcccttt        60 ttttccaca gctcgcggtt gaggacaaac tcttcgcggt ctttccagtg gggatcgacg        120
gtatctgca                                                                129

<210> SEQ ID NO 4
<211> LENGTH: 39
<212> TYPE: DNA
<213> ORGANISM: Artificial
<220> FEATURE:
<223> OTHER INFORMATION: synthetic nucleic acid

<400> SEQUENCE: 4
ggtctgacta actagctagc taagtgagca ggcggccgc                                39

<210> SEQ ID NO 5
<211> LENGTH: 125
<212> TYPE: DNA
<213> ORGANISM: Homo sapiens

<400> SEQUENCE: 5
gaattcttct gacatccggc gggtttctga catccggcgg gtttctgaca tccggcgggt        60
ttctgacatc cggcgggttt ctgacatccg gcgggtgact cacaaccccca gaaacagaca     120 tccat                                                                   125

<210> SEQ ID NO 6
<211> LENGTH: 754
<212> TYPE: DNA
<213> ORGANISM: Artificial
<220> FEATURE:
<223> OTHER INFORMATION: synthetic nucleic acid

<400> SEQUENCE: 6
ggcggccggg agcaatgcac tgcagatgca gctgcaggaa ttcgccacca tggtgagcaa        60
gggcgaggag ctgttcaccg gggtggtgcc catcctggtc gagctggacg gcgacgtaaa      120
cggccacaag ttcagcgtgt ccggcgaggg cgagggcgat gccacctacg gcaagctgac      180
cctgaagttc atctgcacca ccggcaagct gcccgtgccc tggcccaccc tcgtgaccac      240
cctgacctac ggcgtgcagt gcttcagccg ctaccccgac cacatgaagc agcacgactt      300
cttcaagtcc gccatgcccg aaggctacgt ccaggagcgc accatcttct tcaaggacga      360
cggcaactac aagacccgcg ccgaggtgaa gttcgagggc gacaccctgg tgaaccgcat      420
cgagctgaag ggcatcgact tcaaggagga cggcaacatc ctggggcaca gctggagta      480 caactacaac agccacaacg tctatatcat ggccgacaag cagaagaacg gcatcaaggt      540
gaacttcaag atccgccaca acatcgagga cggcagcgtg cagctcgccg accactacca      600
gcagaacacc cccatcggcg acggccccgt gctgctgccc gacaaccact acctgagcac      660
ccagtccgcc ctgagcaaag accccaacga gaagcgcgat cacatggtcc tgctggagtt      720
cgtgaccgcc gccgggatca ctctcggcat ggac                                   754

<210> SEQ ID NO 7
<211> LENGTH: 816
<212> TYPE: DNA
<213> ORGANISM: Simian virus 40

<400> SEQUENCE: 7
gagctgtaca agtaagaatt cgatatcaag cttgcagatc tgcgactcta gaggatctgc        60
gactctagag gatcataatc agccatacca catttgtaga ggttttactt gctttaaaaa      120
```

-continued

```
acctcccaca cctcccctg aacctgaaac ataaaatgaa tgcaattgtt gttgttaact      180
tgtttattgc agcttataat ggttacaaat aaagcaatag catcacaaat ttcacaaata      240
aagcattttt ttcactgcat tctagttgtg gtttgtccaa actcatcaat gtatcttatc      300
atgtctggat ctgcgactct agaggatcat aatcagccat accacatttg tagaggtttt      360
acttgcttta aaaaacctcc cacacctccc cctgaacctg aaacataaaa tgaatgcaat      420
tgttgttgtt aacttgttta ttgcagctta taatggttac aaataaagca atagcatcac      480
aaatttcaca aataaagcat ttttttcact gcattctagt tgtggtttgt ccaaactcat      540
caatgtatct tatcatgtct ggatctgcga ctctagagga tcataatcag ccataccaca      600
tttgtagagg ttttacttgc tttaaaaaac ctcccacacc tcccctgaa cctgaaacat      660 aaaatgaatg caattgttgt tgttaacttg tttattgcag cttataatgg ttacaaataa      720
agcaatagca tcacaaattt cacaaataaa gcatttttt cactgcattc tagttgtggt      780
ttgtccaaac tcatcaatgt atcttatcat gtctgg                              816
```

```
<210> SEQ ID NO 8
<211> LENGTH: 34
<212> TYPE: DNA
<213> ORGANISM: Artificial
<220> FEATURE:
<223> OTHER INFORMATION: synthetic nucleic acid

<400> SEQUENCE: 8
ataacttcgt atagcataca ttatacgaac ggta                                 34

<210> SEQ ID NO 9
<211> LENGTH: 34
<212> TYPE: DNA
<213> ORGANISM: Bacteriophage P1

<400> SEQUENCE: 9
ataacttcgt ataatgtatg ctatacgaag ttat                                 34

<210> SEQ ID NO 10
<211> LENGTH: 34
<212> TYPE: DNA
<213> ORGANISM: Artificial
<220> FEATURE:
<223> OTHER INFORMATION: synthetic nucleic acid

<400> SEQUENCE: 10
ataacttcgt ataatgtata ctatacgaag ttat                                 34

<210> SEQ ID NO 11
<211> LENGTH: 34
<212> TYPE: DNA
<213> ORGANISM: Artificial
<220> FEATURE:
<223> OTHER INFORMATION: synthetic nucleic acid

<400> SEQUENCE: 11
ataacttcgt ataatgtgta ctatacgaag ttat                                 34

<210> SEQ ID NO 12
<211> LENGTH: 34
<212> TYPE: DNA
<213> ORGANISM: Artificial
<220> FEATURE:
<223> OTHER INFORMATION: sythetic nucleic acid
```

-continued

<400> SEQUENCE: 12
ataacttcgt ataaagtatc ctatacgaag ttat                                    34

<210> SEQ ID NO 13
<211> LENGTH: 34
<212> TYPE: DNA
<213> ORGANISM: Artificial
<220> FEATURE:
<223> OTHER INFORMATION: synthetic nucleic acid

<400> SEQUENCE: 13
ataacttcgt ataatgtatg ctatacgaac ggta                                    34

<210> SEQ ID NO 14
<211> LENGTH: 34
<212> TYPE: DNA
<213> ORGANISM: Artificial
<220> FEATURE:
<223> OTHER INFORMATION: synthetic nucleic acid

<400> SEQUENCE: 14
taccgttcgt ataatgtatg ctatacgaag ttat                                    34

<210> SEQ ID NO 15
<211> LENGTH: 40
<212> TYPE: DNA
<213> ORGANISM: Artificial
<220> FEATURE:
<223> OTHER INFORMATION: synthetic oligonucleotide

<400> SEQUENCE: 15
tcgagtaccg ttcgtatagc atacattata cgaagttatc                              40

<210> SEQ ID NO 16
<211> LENGTH: 40
<212> TYPE: DNA
<213> ORGANISM: Artificial
<220> FEATURE:
<223> OTHER INFORMATION: synthetic oligonucleotide

<400> SEQUENCE: 16
tcgagataac ttcgtataat gtatgctata cgaacggtac                              40

<210> SEQ ID NO 17
<211> LENGTH: 40
<212> TYPE: DNA
<213> ORGANISM: Artificial
<220> FEATURE:
<223> OTHER INFORMATION: synthetic oligonucleotide

<400> SEQUENCE: 17
agctttaccg ttcgtataat gtatgctata cgaagttata                              40

<210> SEQ ID NO 18
<211> LENGTH: 40
<212> TYPE: DNA
<213> ORGANISM: Artificial
<220> FEATURE:
<223> OTHER INFORMATION: synthetic oligonucleotide

<400> SEQUENCE: 18
agcttataac ttcgtatagc atacattata cgaacggtaa                              40

<210> SEQ ID NO 19
<211> LENGTH: 52

```
<212> TYPE: DNA
<213> ORGANISM: Artificial
<220> FEATURE:
<223> OTHER INFORMATION: synthetic primer

<400> SEQUENCE: 19
ctgcaggtct gactaactag ctagctaagt gaatatggtc gacctgcagg cg      52

<210> SEQ ID NO 20
<211> LENGTH: 24
<212> TYPE: DNA
<213> ORGANISM: Artificial
<220> FEATURE:
<223> OTHER INFORMATION: synthetic primer

<400> SEQUENCE: 20
ctgcagtgct cccggccgcc atgg                                     24

<210> SEQ ID NO 21
<211> LENGTH: 20
<212> TYPE: DNA
<213> ORGANISM: Artificial
<220> FEATURE:
<223> OTHER INFORMATION: synthetic primer

<400> SEQUENCE: 21
tttctatagg actgaaagac                                          20

<210> SEQ ID NO 22
<211> LENGTH: 20
<212> TYPE: DNA
<213> ORGANISM: Artificial
<220> FEATURE:
<223> OTHER INFORMATION: synthetic primer

<400> SEQUENCE: 22
cctatttttt taattataag                                          20

<210> SEQ ID NO 23
<211> LENGTH: 20
<212> TYPE: DNA
<213> ORGANISM: Artificial
<220> FEATURE:
<223> OTHER INFORMATION: synthetic primer

<400> SEQUENCE: 23
ctatacagag aaatcctgcc                                          20

<210> SEQ ID NO 24
<211> LENGTH: 20
<212> TYPE: DNA
<213> ORGANISM: Artificial
<220> FEATURE:
<223> OTHER INFORMATION: synthetic primer

<400> SEQUENCE: 24
cactctcggc atggacgagc                                          20

<210> SEQ ID NO 25
<211> LENGTH: 20
<212> TYPE: DNA
<213> ORGANISM: Artificial
<220> FEATURE:
```

```
<223> OTHER INFORMATION: synthetic primer

<400> SEQUENCE: 25
cggacacgct gaacttgtgg                                              20
```